(12) United States Patent
Gould et al.

(10) Patent No.: US 7,858,303 B2
(45) Date of Patent: Dec. 28, 2010

(54) METHOD OF ANALYZING BREAST CANCER SUSCEPTIBILITY AND RESISTANCE

(75) Inventors: Michael N. Gould, Madison, WI (US);
Jill D. Haag, Mt. Horeb, WI (US);
David J. Samuelson, Madison, WI (US);
Stephanie E. Nelson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 191 days.

(21) Appl. No.: 11/374,326

(22) Filed: Mar. 13, 2006

(65) Prior Publication Data

US 2006/0240454 A1 Oct. 26, 2006

Related U.S. Application Data

(60) Provisional application No. 60/739,798, filed on Nov. 23, 2005, provisional application No. 60/661,420, filed on Mar. 14, 2005.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................... 435/6; 435/91.2; 536/23.1; 536/23.5

(58) Field of Classification Search ................. None
See application file for complete search history.

(56) References Cited

U.S. PATENT DOCUMENTS

2004/0014097 A1* 1/2004 McGlennen et al. ........... 435/6

OTHER PUBLICATIONS

NCBI Single Nucleotide Polymorphism (SNP) Database. rs2182317, ss3119497, Jun. 7, 2001.*
Hirschhorn et al. Genetics in Medicine. 2002. 4(2): 45-61.*
Pharoah et al. PLoS Genetics. Mar. 2007. 3(3): 0401-0406.*
Young et al. British Journal of Cancer (1999) 81: 141-143.*
Ameyaw et al. Journal of the National Cancer Institute. 2000. 92: 1947.*
Mavaddat et al. Cancer Epidemiol Biomarkers Prev. 2009. 18: 255-259.*
PCT/US2006/008958 International Search Report mailed May 3, 2007.
Lan Hong et al: "Genetic loci controlling breast cancer susceptibility in the Wistar -Kyoto rat", Genetics, vol. 157, No. 1, Jan. 2001, pp. 331-339.
Samuelson David J et al: "Fine mapping reveals multiple loci and a possible epistatic interaction within the mammary carcinoma susceptibility quantitative trait locus, Mcs5", Cancer Research, vol. 65, No. 21, Nov. 2005, pp. 9637-9642.
Cotroneo M S et al: "The Mcs7 quantitative trait locus is associated with an increased susceptibility to mammary cancer in congenic rats and an allele-specific imbalance", Oncogene, vol. 25, No. 36, Aug. 2006, pp. 5011-5017.
Polyak, K.: "Breast cancer gene discovery", Expert Reviews in Molecular Biology, Aug. 2002, pp. 1-18.
Hill et al., "Linkage Disequilibrium in Finite Populations", Theoretical and Applied Genetics, 38, 226-231, 1968.
VanLiere et al., "Mathematical Properties of the r2 Measure of Linkage Disequilibrium", Theoretical Population Biology, 74, 130-137, 2008.
Samuelson et al., "Rat Mcs5a is a Compound Quantitative Trait Locus with Orthologous Human Loci that Associate with Breast Cancer Risk", PNAS, 104, 15, 6299-6304, 2007.

* cited by examiner

*Primary Examiner*—Carla Myers
(74) *Attorney, Agent, or Firm*—Quarles & Brady, LLP

(57) ABSTRACT

A method of analyzing breast cancer susceptibility or resistance, comprising the steps of obtaining a DNA sample from a patient, genotyping the sample for the presence of the minor allele of single nucleotide polymorphisms rs6476643 or rs2182317, and correlating the identity of the allele with risk assessment data is disclosed.

5 Claims, 2 Drawing Sheets

SEQUENCE LISTING

<160> NUMBER OF SEQ ID NOS: 185

<210> SEQ ID NO 1
<211> LENGTH: 269
<212> TYPE: DNA
<213> ORGANISM: Homo sapiens

<400> SEQUENCE: 1
aaaatcttaa tcaaatgtct ctttgtgtac attcctttat gtatacagta tcaaacattt      60
tagacgagtg ggaaactaat aatcactaaa ctaaaagaaa gagggtaatg agagaaatta     120
gcagacattt caaacaaaac ccatgacagg taactcaaga ataggttcat tcattaaggc     180
aaactgaaag aacaaaacac ttgttccatc tatttcctga ctgaagcagg tacaaggaat     240
ttgtttactt cacatcttcc tgtgaaaag                                        269

<210> SEQ ID NO 2
<211> LENGTH: 200
<212> TYPE: DNA
<213> ORGANISM: Homo sapiens
<220> FEATURE:
<221> NAME/KEY: variation
<222> LOCATION: (117)..(117)
<223> OTHER INFORMATION: y is c or t

<400> SEQUENCE: 2
aaaaacacaa aaaccaaagg cttccagatg aggacagaat tccattttac ccttcacttc    60
tacacaaata ggcaaaatta gaagtggaac actcgtgttt atctgcctcc aggtcayagc   120
atcacagcag agtagaagga gcagtggctt ggcattgctg agaaccaaaa ataatgagca   180
gtttcgccac tgacaaggca                                              200

<210> SEQ ID NO 3
<211> LENGTH: 217
<212> TYPE: DNA
<213> ORGANISM: Homo sapiens
<220> FEATURE:
<221> NAME/KEY: variation
<222> LOCATION: (169)..(169)
<223> OTHER INFORMATION: r is a or g

<400> SEQUENCE: 3
aagaggattt ctttggagga agcagctggt gtgctaagtg ccgctcatgg ccccagggga    60
taaggaaggg gtgtgtgggt gcctatctca cctcacttca gcaggaccac tcagagcttg   120
agctgtgtct cctgcagttg ggggcccagg ggactgggtc tgactcccrc cctggaaatt   180
tacaggaaaa gagcagggct ggctaatgct ttggctg                            217

<210> SEQ ID NO 4
<211> LENGTH: 214
<212> TYPE: DNA
<213> ORGANISM: Homo sapiens
<220> FEATURE:
<221> NAME/KEY: variation
<222> LOCATION: (116)..(116)
<223> OTHER INFORMATION: k is t or g

<400> SEQUENCE: 4
cagagaaaaa gaaaggagga ggaggaggaa agagaagtca agttttaaaa gcaaacagaa    60
ataatagttt tgatgggatg gatttgtttt cttaataagc ctaatgatcc caggaktctc   120
attggattat tagcaactgt atttaaaatt taaatctaaa acaagttttg tagctgcaaa   180
gtgcttatca gaacctaacc atgcctctct ggct                              214

<210> SEQ ID NO 5
<211> LENGTH: 200
<212> TYPE: DNA
<213> ORGANISM: Homo sapiens
<220> FEATURE:
<221> NAME/KEY: variation
<222> LOCATION: (70)..(70)
<223> OTHER INFORMATION: y is c or t

<400> SEQUENCE: 5
agagctcagt ttcccaaata aacctgaatc tgaatcccat ttaccagctc tgtgacctca    60
taccagtcgy ttgaattctc tgagcttgcc tcagtttcat ctgtgaagtg gggattgtca   120
tgtgtgtcct gcctaactca agcagctgtt gagagaataa gatgagatga ttgctctgtt   180
tggtgtttta caaactgaaa                                              200

<210> SEQ ID NO 6
<211> LENGTH: 236
<212> TYPE: DNA
<213> ORGANISM: Homo sapiens
<220> FEATURE:
<221> NAME/KEY: variation
<222> LOCATION: (218)..(218)
<223> OTHER INFORMATION: r is a or g

<400> SEQUENCE: 6

```
tagtgctaga gagggtggca tctgccccccg ggggctgtgg ggagcacggt ggtagtgggg      60
agttgcagtc acccagcaga tgcaaagcag aatgaagcct atgggaagtg ccagatgta      120 gttgtcaaga ccagggtagg gccacacttg atgctggcca caacctcaag acatgccttc     180
ttctggggag ctgatctccc aggagctgag ccagcagraa aaaaaaaaaa agagag         236
```

```
<210> SEQ ID NO 7
<211> LENGTH: 224
<212> TYPE: DNA
<213> ORGANISM: Homo sapiens
<220> FEATURE:
<221> NAME/KEY: variation
<222> LOCATION: (77)..(77)
<223> OTHER INFORMATION: r is a or g

<400> SEQUENCE: 7
aggctgacac tgacgcaggt agctaggaaa tggaggggga cagggcaaaa ttccatgggg      60
aacatttgta ctcaccrgac aagagaatag ttcttatctt actttctgac aagtgctatg    120 cttttggtg tttaactgcc ttggagagag taatttgatg attaatcttt atctacaaaa     180 taattttaa aattaaactt tattttgaga aaattgtaga ttca                       224
```

```
<210> SEQ ID NO 8
<211> LENGTH: 200
<212> TYPE: DNA
<213> ORGANISM: Homo sapiens
<220> FEATURE:
<221> NAME/KEY: variation
<222> LOCATION: (66)..(66)
<223> OTHER INFORMATION: r is a or g

<400> SEQUENCE: 8
aagtgctgct agtcttcccc caccgcccctt ggatgaagga tgcacttgtt aacatctgcc    60
tgtgcrccat ccccagaatg atctaacatc ccagtctgat ggtgcctcaa ccctactcag   120
aactcctccc atgaacctgc cagtgcactg ggaacacggt gcaaactcct tgaccaggaa    180
ttggcccctg ctgactcccc                                                200
```

```
<210> SEQ ID NO 9
<211> LENGTH: 200
<212> TYPE: DNA
<213> ORGANISM: Homo sapiens
<220> FEATURE:
<221> NAME/KEY: variation
<222> LOCATION: (152)..(152)
<223> OTHER INFORMATION: r is a or g

<400> SEQUENCE: 9
aggtggtgag gaatagaaag gctatgtgta ggtcaaggag ctggtacgag caaggaactg     60
gtgagagctg ggagagcatg agacagatga gagcagtgag cctggtggaa gcacagaaa    120 ggcagagcac ttcagagaca gggcagcggg argaggctct ggaggctctg aacctgggct   180
ggaatcctcg ctggctgtgg                                                200
```

```
<210> SEQ ID NO 10
<211> LENGTH: 200
<212> TYPE: DNA
<213> ORGANISM: Homo sapiens
<220> FEATURE:
<221> NAME/KEY: variation
<222> LOCATION: (43)..(43)
<223> OTHER INFORMATION: y is c or t
```

-continued

<400> SEQUENCE: 10
atttctctta aagaacagtg attttaaagt aggtttaaac aaygggttta aagaacagtg    60
attttccatt ttgacaaggc ttgtttggta tagccacttc aaaatatccc cacatcaaaa   120
tatgatgctt tatctgggat atcttttcca gactttggga gccttccctc ctgcactttc   180
atttctgcaa ggcaatactc                                               200

<210> SEQ ID NO 11
<211> LENGTH: 400
<212> TYPE: DNA
<213> ORGANISM: Homo sapiens
<220> FEATURE:
<221> NAME/KEY: variation
<222> LOCATION: (213)..(213)
<223> OTHER INFORMATION: w is t or a

<400> SEQUENCE: 11
caacatattt gtaatacaga catcgaaaat aaaccaaata tccagcaata gggacttagc    60
tttaaaaatg gcactcttat ctatagcaaa taaacaataa tgttgtagaa taataaagac   120
acagggaaat gtttacagtg tatatttttc agtttagaaa ccagcatata tggtaagttc   180
ccaattatgt tgaaaatgtg tcttttcaca cwaaaagact ggaagagtaa ttagcaactt   240
atagctttta gtggacaatt tttattatct tctctccaaa aaagaaaact ttcaaaattt   300
tctaccagcc acatgtatta ctttataag agggaggaaa taagtgacaa ttaagaaaaa    360
gagataagct tttggagagc gttgtttgag cgtcactagg                         400

<210> SEQ ID NO 12
<211> LENGTH: 400
<212> TYPE: DNA
<213> ORGANISM: Homo sapiens
<220> FEATURE:
<221> NAME/KEY: variation
<222> LOCATION: (174)..(174)
<223> OTHER INFORMATION: r is a or g

<400> SEQUENCE: 12
tggaaaacta aatgagcaca tcatttatct tgcaaattcc agacaggtgg tgttttcaga    60
aggaagagtg gtcttaggtc catttgtgtg agtatattta tagaagtgaa agctttgggg   120
gaaggaaata gattgatttt ttttcccctt gaacttctga aattattttt tccrctccat   180
ttgtaattga gcccagggag ctattcttat ttcttccttt cttgggcact gcgttagacc   240
taaaaatgtt aactggctta ggatgtgggt tttgctaaaa tgattcccct tgaagtcttc   300
actgggcttt ctcatgctta aaagtggggt cccgcagaag atcactttct acctaatgca   360
ctttgctcct gaagtctttg gcaacgttgg ggtggtcaga                         400

<210> SEQ ID NO 13
<211> LENGTH: 20
<212> TYPE: DNA
<213> ORGANISM: Artificial
<220> FEATURE:
<223> OTHER INFORMATION: Synthetic oligonucleotide

<400> SEQUENCE: 13
gacttaatgt ggggagtgaa                                                20

<210> SEQ ID NO 14
<211> LENGTH: 20
<212> TYPE: DNA
<213> ORGANISM: Artificial

```
<220> FEATURE:
<223> OTHER INFORMATION: Synthetic oligonucleotide

<400> SEQUENCE: 14
agcacatatg gaggtttgac                                                 20

<210> SEQ ID NO 15
<211> LENGTH: 20
<212> TYPE: DNA
<213> ORGANISM: Artificial
<220> FEATURE:
<223> OTHER INFORMATION: Synthetic oligonucleotide

<400> SEQUENCE: 15
ctagaaaggt gctttggttg                                                 20

<210> SEQ ID NO 16
<211> LENGTH: 18
<212> TYPE: DNA
<213> ORGANISM: Artificial
<220> FEATURE:
<223> OTHER INFORMATION: Synthetic oligonucleotide

<400> SEQUENCE: 16
tcagcttctc ctccttcc                                                   18

<210> SEQ ID NO 17
<211> LENGTH: 20
<212> TYPE: DNA
<213> ORGANISM: Artificial
<220> FEATURE:
<223> OTHER INFORMATION: Synthetic oligonucleotide

<400> SEQUENCE: 17
ccagtctgat gacctgagtt                                                 20

<210> SEQ ID NO 18
<211> LENGTH: 20
<212> TYPE: DNA
<213> ORGANISM: Artificial
<220> FEATURE:
<223> OTHER INFORMATION: Synthetic oligonucleotide

<400> SEQUENCE: 18
cttgcatgtg tgtaagtgct                                                 20

<210> SEQ ID NO 19
<211> LENGTH: 27
<212> TYPE: DNA
<213> ORGANISM: Artificial
<220> FEATURE:
<223> OTHER INFORMATION: Synthetic oligonucleotide

<400> SEQUENCE: 19
aggcctcatc acagaaaacg tcatccg                                         27

<210> SEQ ID NO 20
<211> LENGTH: 20
<212> TYPE: DNA
<213> ORGANISM: Artificial
<220> FEATURE:
<223> OTHER INFORMATION: Synthetic oligonucleotide

<400> SEQUENCE: 20
gctggcatag cagtgaacga                                                 20
```

```
<210> SEQ ID NO 21
<211> LENGTH: 22
<212> TYPE: DNA
<213> ORGANISM: Artificial
<220> FEATURE:
<223> OTHER INFORMATION: Synthetic oligonucleotide

<400> SEQUENCE: 21
ctacacctcc ccactggttc tc                                              22

<210> SEQ ID NO 22
<211> LENGTH: 18
<212> TYPE: DNA
<213> ORGANISM: Artificial
<220> FEATURE:
<223> OTHER INFORMATION: Synthetic oligonucleotide

<400> SEQUENCE: 22
cttttcccag accacatc                                                   18

<210> SEQ ID NO 23
<211> LENGTH: 21
<212> TYPE: DNA
<213> ORGANISM: Artificial
<220> FEATURE:
<223> OTHER INFORMATION: Synthetic oligonucleotide

<400> SEQUENCE: 23
ccagcctcta tgatcgaatc g                                               21

<210> SEQ ID NO 24
<211> LENGTH: 24
<212> TYPE: DNA
<213> ORGANISM: Artificial
<220> FEATURE:
<223> OTHER INFORMATION: Synthetic oligonucleotide

<400> SEQUENCE: 24
cattctcaaa gttgcagttg tcaa                                            24

<210> SEQ ID NO 25
<211> LENGTH: 18
<212> TYPE: DNA
<213> ORGANISM: Artificial
<220> FEATURE:
<223> OTHER INFORMATION: Synthetic oligonucleotide

<400> SEQUENCE: 25
cctttccacc acctgctg                                                   18

<210> SEQ ID NO 26
<211> LENGTH: 21
<212> TYPE: DNA
<213> ORGANISM: Artificial
<220> FEATURE:
<223> OTHER INFORMATION: Synthetic oligonucleotide

<400> SEQUENCE: 26
cgcctacacc ttttgcatga g                                               21

<210> SEQ ID NO 27
<211> LENGTH: 21
<212> TYPE: DNA
<213> ORGANISM: Artificial
<220> FEATURE:
<223> OTHER INFORMATION: Synthetic oligonucleotide
```

<400> SEQUENCE: 27
gcgggagtcc tgtgattctt c                                              21

<210> SEQ ID NO 28
<211> LENGTH: 30
<212> TYPE: DNA
<213> ORGANISM: Artificial
<220> FEATURE:
<223> OTHER INFORMATION: Synthetic oligonucleotide

<400> SEQUENCE: 28
agaacactct tcttcctttt aggtaaatgg                                     30

<210> SEQ ID NO 29
<211> LENGTH: 24
<212> TYPE: DNA
<213> ORGANISM: Artificial
<220> FEATURE:
<223> OTHER INFORMATION: Synthetic oligonucleotide

<400> SEQUENCE: 29
tgtgctttcc gtgtctggaa taaa                                           24

<210> SEQ ID NO 30
<211> LENGTH: 16
<212> TYPE: DNA
<213> ORGANISM: Artificial
<220> FEATURE:
<223> OTHER INFORMATION: Synthetic oligonucleotide

<400> SEQUENCE: 30
aagagctgga gaccag                                                    16

<210> SEQ ID NO 31
<211> LENGTH: 15
<212> TYPE: DNA
<213> ORGANISM: Artificial
<220> FEATURE:
<223> OTHER INFORMATION: Synthetic oligonucleotide

<400> SEQUENCE: 31
agagctggag cccag                                                     15

<210> SEQ ID NO 32
<211> LENGTH: 33
<212> TYPE: DNA
<213> ORGANISM: Artificial
<220> FEATURE:
<223> OTHER INFORMATION: Synthetic oligonucleotide

<400> SEQUENCE: 32
acaggatgac atagtgaagc tcttattaaa aat                                 33

<210> SEQ ID NO 33
<211> LENGTH: 30
<212> TYPE: DNA
<213> ORGANISM: Artificial
<220> FEATURE:
<223> OTHER INFORMATION: Synthetic oligonucleotide

<400> SEQUENCE: 33
acacaattta aaataacttg aggcagcaag                                     30

<210> SEQ ID NO 34

```
<211> LENGTH: 21
<212> TYPE: DNA
<213> ORGANISM: Artificial
<220> FEATURE:
<223> OTHER INFORMATION: Synthetic oligonucleotide

<400> SEQUENCE: 34
ctctagattt ccattagtat c                                              21

<210> SEQ ID NO 35
<211> LENGTH: 21
<212> TYPE: DNA
<213> ORGANISM: Artificial
<220> FEATURE:
<223> OTHER INFORMATION: Synthetic oligonucleotide

<400> SEQUENCE: 35
ctctagattt ccaatagtat c                                              21

<210> SEQ ID NO 36
<211> LENGTH: 23
<212> TYPE: DNA
<213> ORGANISM: Artificial
<220> FEATURE:
<223> OTHER INFORMATION: Synthetic oligonucleotide

<400> SEQUENCE: 36
ttcaggagct tgcagtctag ttg                                            23

<210> SEQ ID NO 37
<211> LENGTH: 23
<212> TYPE: DNA
<213> ORGANISM: Artificial
<220> FEATURE:
<223> OTHER INFORMATION: Synthetic oligonucleotide

<400> SEQUENCE: 37
tttcatcctg ccttggacaa tca                                            23

<210> SEQ ID NO 38
<211> LENGTH: 15
<212> TYPE: DNA
<213> ORGANISM: Artificial
<220> FEATURE:
<223> OTHER INFORMATION: Synthetic oligonucleotide

<400> SEQUENCE: 38
acgtccaccg tccct                                                     15

<210> SEQ ID NO 39
<211> LENGTH: 15
<212> TYPE: DNA
<213> ORGANISM: Artificial
<220> FEATURE:
<223> OTHER INFORMATION: Synthetic oligonucleotide

<400> SEQUENCE: 39
acgtccaccc tccct                                                     15

<210> SEQ ID NO 40
<211> LENGTH: 26
<212> TYPE: DNA
<213> ORGANISM: Artificial
<220> FEATURE:
<223> OTHER INFORMATION: Synthetic oligonucleotide

<400> SEQUENCE: 40
```

-continued

```
tctgcaacag ctatcaaagt ttctgt                                          26

<210> SEQ ID NO 41
<211> LENGTH: 25
<212> TYPE: DNA
<213> ORGANISM: Artificial
<220> FEATURE:
<223> OTHER INFORMATION: Synthetic oligonucleotide

<400> SEQUENCE: 41
atgcattttg gaacagtgct ttcat                                           25

<210> SEQ ID NO 42
<211> LENGTH: 17
<212> TYPE: DNA
<213> ORGANISM: Artificial
<220> FEATURE:
<223> OTHER INFORMATION: Synthetic oligonucleotide

<400> SEQUENCE: 42
aaagccaggt gtatcta                                                    17

<210> SEQ ID NO 43
<211> LENGTH: 17
<212> TYPE: DNA
<213> ORGANISM: Artificial
<220> FEATURE:
<223> OTHER INFORMATION: Synthetic oligonucleotide

<400> SEQUENCE: 43
aaagccaggt atatcta                                                    17

<210> SEQ ID NO 44
<211> LENGTH: 25
<212> TYPE: DNA
<213> ORGANISM: Artificial
<220> FEATURE:
<223> OTHER INFORMATION: Synthetic oligonucleotide

<400> SEQUENCE: 44
cccctctgaa cagagccatt ttata                                           25

<210> SEQ ID NO 45
<211> LENGTH: 21
<212> TYPE: DNA
<213> ORGANISM: Artificial
<220> FEATURE:
<223> OTHER INFORMATION: Synthetic oligonucleotide

<400> SEQUENCE: 45
ccacctctgt ttccgctaga a                                               21

<210> SEQ ID NO 46
<211> LENGTH: 21
<212> TYPE: DNA
<213> ORGANISM: Artificial
<220> FEATURE:
<223> OTHER INFORMATION: Synthetic oligonucleotide

<400> SEQUENCE: 46
cattaatgtt caattgaatt t                                               21

<210> SEQ ID NO 47
<211> LENGTH: 20
<212> TYPE: DNA
```

```
<213> ORGANISM: Artificial
<220> FEATURE:
<223> OTHER INFORMATION: Synthetic oligonucleotide

<400> SEQUENCE: 47
attaatgttc aatcgaattt                                             20

<210> SEQ ID NO 48
<211> LENGTH: 25
<212> TYPE: DNA
<213> ORGANISM: Artificial
<220> FEATURE:
<223> OTHER INFORMATION: Synthetic oligonucleotide

<400> SEQUENCE: 48
cgtttgaaat gtgaatgcag tctga                                       25

<210> SEQ ID NO 49
<211> LENGTH: 23
<212> TYPE: DNA
<213> ORGANISM: Artificial
<220> FEATURE:
<223> OTHER INFORMATION: Synthetic oligonucleotide

<400> SEQUENCE: 49
gtgctttcca acatagggca aaa                                         23

<210> SEQ ID NO 50
<211> LENGTH: 15
<212> TYPE: DNA
<213> ORGANISM: Artificial
<220> FEATURE:
<223> OTHER INFORMATION: Synthetic oligonucleotide

<400> SEQUENCE: 50
tctccaacaa aatac                                                  15

<210> SEQ ID NO 51
<211> LENGTH: 17
<212> TYPE: DNA
<213> ORGANISM: Artificial
<220> FEATURE:
<223> OTHER INFORMATION: Synthetic oligonucleotide

<400> SEQUENCE: 51
catctccaat aaaatac                                                17

<210> SEQ ID NO 52
<211> LENGTH: 25
<212> TYPE: DNA
<213> ORGANISM: Artificial
<220> FEATURE:
<223> OTHER INFORMATION: Synthetic oligonucleotide

<400> SEQUENCE: 52
ggagtattgc cttgcagaaa tgaaa                                       25

<210> SEQ ID NO 53
<211> LENGTH: 29
<212> TYPE: DNA
<213> ORGANISM: Artificial
<220> FEATURE:
<223> OTHER INFORMATION: Synthetic oligonucleotide

<400> SEQUENCE: 53
ccccacatca aaatatgatg ctttatctg                                   29
```

<210> SEQ ID NO 54
<211> LENGTH: 16
<212> TYPE: DNA
<213> ORGANISM: Artificial
<220> FEATURE:
<223> OTHER INFORMATION: Synthetic oligonucleotide

<400> SEQUENCE: 54
ccagactttg ggagcc                                            16

<210> SEQ ID NO 55
<211> LENGTH: 15
<212> TYPE: DNA
<213> ORGANISM: Artificial
<220> FEATURE:
<223> OTHER INFORMATION: Synthetic oligonucleotide

<400> SEQUENCE: 55
cagacttcgg gagcc                                             15

<210> SEQ ID NO 56
<211> LENGTH: 25
<212> TYPE: DNA
<213> ORGANISM: Artificial
<220> FEATURE:
<223> OTHER INFORMATION: Synthetic oligonucleotide

<400> SEQUENCE: 56
ccttgtatgg gtttaggatg cagat                                  25

<210> SEQ ID NO 57
<211> LENGTH: 24
<212> TYPE: DNA
<213> ORGANISM: Artificial
<220> FEATURE:
<223> OTHER INFORMATION: Synthetic oligonucleotide

<400> SEQUENCE: 57
cccacagaga gtctttagct tcac                                   24

<210> SEQ ID NO 58
<211> LENGTH: 18
<212> TYPE: DNA
<213> ORGANISM: Artificial
<220> FEATURE:
<223> OTHER INFORMATION: Synthetic oligonucleotide

<400> SEQUENCE: 58
agttggtgct ttgaccta                                          18

<210> SEQ ID NO 59
<211> LENGTH: 16
<212> TYPE: DNA
<213> ORGANISM: Artificial
<220> FEATURE:
<223> OTHER INFORMATION: Synthetic oligonucleotide

<400> SEQUENCE: 59
ttggtgcctt gaccta                                            16

<210> SEQ ID NO 60
<211> LENGTH: 25
<212> TYPE: DNA
<213> ORGANISM: Artificial
<220> FEATURE:

<223> OTHER INFORMATION: Synthetic oligonucleotide

<400> SEQUENCE: 60
tcctactaaa cagaagcccc ttgta        25

<210> SEQ ID NO 61
<211> LENGTH: 25
<212> TYPE: DNA
<213> ORGANISM: Artificial
<220> FEATURE:
<223> OTHER INFORMATION: Synthetic oligonucleotide

<400> SEQUENCE: 61
ccaacatccc ccagttactt tcatt        25

<210> SEQ ID NO 62
<211> LENGTH: 21
<212> TYPE: DNA
<213> ORGANISM: Artificial
<220> FEATURE:
<223> OTHER INFORMATION: Synthetic oligonucleotide

<400> SEQUENCE: 62
atttactctg cttattcctg t        21

<210> SEQ ID NO 63
<211> LENGTH: 21
<212> TYPE: DNA
<213> ORGANISM: Artificial
<220> FEATURE:
<223> OTHER INFORMATION: Synthetic oligonucleotide

<400> SEQUENCE: 63
atttactctg cttatgcctg t        21

<210> SEQ ID NO 64
<211> LENGTH: 25
<212> TYPE: DNA
<213> ORGANISM: Artificial
<220> FEATURE:
<223> OTHER INFORMATION: Synthetic oligonucleotide

<400> SEQUENCE: 64
cattcggtgt ccagagattt ctgta        25

<210> SEQ ID NO 65
<211> LENGTH: 25
<212> TYPE: DNA
<213> ORGANISM: Artificial
<220> FEATURE:
<223> OTHER INFORMATION: Synthetic oligonucleotide

<400> SEQUENCE: 65
cctgtggaaa tcaaggcttc actta        25

<210> SEQ ID NO 66
<211> LENGTH: 17
<212> TYPE: DNA
<213> ORGANISM: Artificial
<220> FEATURE:
<223> OTHER INFORMATION: Synthetic oligonucleotide

<400> SEQUENCE: 66
cctggaattc tgctgct        17

```
<210> SEQ ID NO 67
<211> LENGTH: 16
<212> TYPE: DNA
<213> ORGANISM: Artificial
<220> FEATURE:
<223> OTHER INFORMATION: Synthetic oligonucleotide

<400> SEQUENCE: 67
ctggaattcc gctgct                                                    16

<210> SEQ ID NO 68
<211> LENGTH: 23
<212> TYPE: DNA
<213> ORGANISM: Artificial
<220> FEATURE:
<223> OTHER INFORMATION: Synthetic oligonucleotide

<400> SEQUENCE: 68
cagccatgta gagagaccag att                                            23

<210> SEQ ID NO 69
<211> LENGTH: 25
<212> TYPE: DNA
<213> ORGANISM: Artificial
<220> FEATURE:
<223> OTHER INFORMATION: Synthetic oligonucleotide

<400> SEQUENCE: 69
ggttttaccc tcccattgtg tagac                                          25

<210> SEQ ID NO 70
<211> LENGTH: 16
<212> TYPE: DNA
<213> ORGANISM: Artificial
<220> FEATURE:
<223> OTHER INFORMATION: Synthetic oligonucleotide

<400> SEQUENCE: 70
actgagcttc agttcc                                                    16

<210> SEQ ID NO 71
<211> LENGTH: 15
<212> TYPE: DNA
<213> ORGANISM: Artificial
<220> FEATURE:
<223> OTHER INFORMATION: Synthetic oligonucleotide

<400> SEQUENCE: 71
ctgagcttcg gttcc                                                     15

<210> SEQ ID NO 72
<211> LENGTH: 23
<212> TYPE: DNA
<213> ORGANISM: Artificial
<220> FEATURE:
<223> OTHER INFORMATION: Synthetic oligonucleotide

<400> SEQUENCE: 72
ggagaagcca tactgaagtg cat                                            23

<210> SEQ ID NO 73
<211> LENGTH: 31
<212> TYPE: DNA
<213> ORGANISM: Artificial
<220> FEATURE:
<223> OTHER INFORMATION: Synthetic oligonucleotide
```

<400> SEQUENCE: 73
ccttattgcc ctaatgtttt actacaaatg c                           31

<210> SEQ ID NO 74
<211> LENGTH: 18
<212> TYPE: DNA
<213> ORGANISM: Artificial
<220> FEATURE:
<223> OTHER INFORMATION: Synthetic oligonucleotide

<400> SEQUENCE: 74
ccttgacatc tccttaaa                                          18

<210> SEQ ID NO 75
<211> LENGTH: 17
<212> TYPE: DNA
<213> ORGANISM: Artificial
<220> FEATURE:
<223> OTHER INFORMATION: Synthetic oligonucleotide

<400> SEQUENCE: 75
cttgacatct gcttaaa                                           17

<210> SEQ ID NO 76
<211> LENGTH: 20
<212> TYPE: DNA
<213> ORGANISM: Artificial
<220> FEATURE:
<223> OTHER INFORMATION: Synthetic oligonucleotide

<400> SEQUENCE: 76
gcatggcaag tgtccaagga                                        20

<210> SEQ ID NO 77
<211> LENGTH: 23
<212> TYPE: DNA
<213> ORGANISM: Artificial
<220> FEATURE:
<223> OTHER INFORMATION: Synthetic oligonucleotide

<400> SEQUENCE: 77
tgtccaaatc ccacccaatc ttt                                    23

<210> SEQ ID NO 78
<211> LENGTH: 15
<212> TYPE: DNA
<213> ORGANISM: Artificial
<220> FEATURE:
<223> OTHER INFORMATION: Synthetic oligonucleotide

<400> SEQUENCE: 78
cagagtcata aagcc                                             15

<210> SEQ ID NO 79
<211> LENGTH: 14
<212> TYPE: DNA
<213> ORGANISM: Artificial
<220> FEATURE:
<223> OTHER INFORMATION: Synthetic oligonucleotide

<400> SEQUENCE: 79
agagtcgtaa agcc                                              14

<210> SEQ ID NO 80
<211> LENGTH: 25

<212> TYPE: DNA
<213> ORGANISM: Artificial
<220> FEATURE:
<223> OTHER INFORMATION: Synthetic oligonucleotide

<400> SEQUENCE: 80
cggttatctc atgtccaaag ctcat             25

<210> SEQ ID NO 81
<211> LENGTH: 25
<212> TYPE: DNA
<213> ORGANISM: Artificial
<220> FEATURE:
<223> OTHER INFORMATION: Synthetic oligonucleotide

<400> SEQUENCE: 81
ccacactatc aatatgcctg cttct             25

<210> SEQ ID NO 82
<211> LENGTH: 16
<212> TYPE: DNA
<213> ORGANISM: Artificial
<220> FEATURE:
<223> OTHER INFORMATION: Synthetic oligonucleotide

<400> SEQUENCE: 82
cagcacatta aaagaa                       16

<210> SEQ ID NO 83
<211> LENGTH: 16
<212> TYPE: DNA
<213> ORGANISM: Artificial
<220> FEATURE:
<223> OTHER INFORMATION: Synthetic oligonucleotide

<400> SEQUENCE: 83
cagcacatta gaagaa                       16

<210> SEQ ID NO 84
<211> LENGTH: 27
<212> TYPE: DNA
<213> ORGANISM: Artificial
<220> FEATURE:
<223> OTHER INFORMATION: Synthetic oligonucleotide

<400> SEQUENCE: 84
tcgaacatcc cataaagctc atttctt           27

<210> SEQ ID NO 85
<211> LENGTH: 19
<212> TYPE: DNA
<213> ORGANISM: Artificial
<220> FEATURE:
<223> OTHER INFORMATION: Synthetic oligonucleotide

<400> SEQUENCE: 85
tggaaagccc agcggaatt                    19

<210> SEQ ID NO 86
<211> LENGTH: 19
<212> TYPE: DNA
<213> ORGANISM: Artificial
<220> FEATURE:
<223> OTHER INFORMATION: Synthetic oligonucleotide

<400> SEQUENCE: 86

```
ccactttgaa gtgttctgt                                              19

<210> SEQ ID NO 87
<211> LENGTH: 18
<212> TYPE: DNA
<213> ORGANISM: Artificial
<220> FEATURE:
<223> OTHER INFORMATION: Synthetic oligonucleotide

<400> SEQUENCE: 87
cactttgaag tattctgt                                               18

<210> SEQ ID NO 88
<211> LENGTH: 22
<212> TYPE: DNA
<213> ORGANISM: Artificial
<220> FEATURE:
<223> OTHER INFORMATION: Synthetic oligonucleotide

<400> SEQUENCE: 88
cttacgaacc tgaaggccaa ag                                          22

<210> SEQ ID NO 89
<211> LENGTH: 17
<212> TYPE: DNA
<213> ORGANISM: Artificial
<220> FEATURE:
<223> OTHER INFORMATION: Synthetic oligonucleotide

<400> SEQUENCE: 89
gggcctgtcg tcatcct                                                17

<210> SEQ ID NO 90
<211> LENGTH: 18
<212> TYPE: DNA
<213> ORGANISM: Artificial
<220> FEATURE:
<223> OTHER INFORMATION: Synthetic oligonucleotide

<400> SEQUENCE: 90
tgttgactca gactcgga                                               18

<210> SEQ ID NO 91
<211> LENGTH: 16
<212> TYPE: DNA
<213> ORGANISM: Artificial
<220> FEATURE:
<223> OTHER INFORMATION: Synthetic oligonucleotide

<400> SEQUENCE: 91
ttgactcgga ctcgga                                                 16

<210> SEQ ID NO 92
<211> LENGTH: 22
<212> TYPE: DNA
<213> ORGANISM: Artificial
<220> FEATURE:
<223> OTHER INFORMATION: Synthetic oligonucleotide

<400> SEQUENCE: 92
cgcagtcaaa ccagacatca tc                                          22

<210> SEQ ID NO 93
<211> LENGTH: 25
<212> TYPE: DNA
<213> ORGANISM: Artificial
```

```
<220> FEATURE:
<223> OTHER INFORMATION: Synthetic oligonucleotide

<400> SEQUENCE: 93
caagatactg ccctttgtgg gatat                                              25

<210> SEQ ID NO 94
<211> LENGTH: 18
<212> TYPE: DNA
<213> ORGANISM: Artificial
<220> FEATURE:
<223> OTHER INFORMATION: Synthetic oligonucleotide

<400> SEQUENCE: 94
tgtagaaccc tgacaatg                                                      18

<210> SEQ ID NO 95
<211> LENGTH: 16
<212> TYPE: DNA
<213> ORGANISM: Artificial
<220> FEATURE:
<223> OTHER INFORMATION: Synthetic oligonucleotide

<400> SEQUENCE: 95
tagaaccccg acaatg                                                        16

<210> SEQ ID NO 96
<211> LENGTH: 25
<212> TYPE: DNA
<213> ORGANISM: Artificial
<220> FEATURE:
<223> OTHER INFORMATION: Synthetic oligonucleotide

<400> SEQUENCE: 96
gcaatgtctt accccaaagc aagat                                              25

<210> SEQ ID NO 97
<211> LENGTH: 21
<212> TYPE: DNA
<213> ORGANISM: Artificial
<220> FEATURE:
<223> OTHER INFORMATION: Synthetic oligonucleotide

<400> SEQUENCE: 97
tgagggtcct ggaggtattc g                                                  21

<210> SEQ ID NO 98
<211> LENGTH: 15
<212> TYPE: DNA
<213> ORGANISM: Artificial
<220> FEATURE:
<223> OTHER INFORMATION: Synthetic oligonucleotide

<400> SEQUENCE: 98
ccccatcatc tcatc                                                         15

<210> SEQ ID NO 99
<211> LENGTH: 15
<212> TYPE: DNA
<213> ORGANISM: Artificial
<220> FEATURE:
<223> OTHER INFORMATION: Synthetic oligonucleotide

<400> SEQUENCE: 99
ccccatcgtc tcatc                                                         15
```

<210> SEQ ID NO 100
<211> LENGTH: 32
<212> TYPE: DNA
<213> ORGANISM: Artificial
<220> FEATURE:
<223> OTHER INFORMATION: Synthetic oligonucleotide

<400> SEQUENCE: 100
agactcagta cattattaga aatgcctttc ac                                     32

<210> SEQ ID NO 101
<211> LENGTH: 28
<212> TYPE: DNA
<213> ORGANISM: Artificial
<220> FEATURE:
<223> OTHER INFORMATION: Synthetic oligonucleotide

<400> SEQUENCE: 101
atggaaatgt caacttcatt gtccctat                                          28

<210> SEQ ID NO 102
<211> LENGTH: 24
<212> TYPE: DNA
<213> ORGANISM: Artificial
<220> FEATURE:
<223> OTHER INFORMATION: Synthetic oligonucleotide

<400> SEQUENCE: 102
aactgtttta tttgttaaat gtta                                              24

<210> SEQ ID NO 103
<211> LENGTH: 22
<212> TYPE: DNA
<213> ORGANISM: Artificial
<220> FEATURE:
<223> OTHER INFORMATION: Synthetic oligonucleotide

<400> SEQUENCE: 103
ctgttttatt tgttagatgt ta                                                22

<210> SEQ ID NO 104
<211> LENGTH: 20
<212> TYPE: DNA
<213> ORGANISM: Artificial
<220> FEATURE:
<223> OTHER INFORMATION: Synthetic oligonucleotide

<400> SEQUENCE: 104
cacagcacag gtgtgacttg                                                   20

<210> SEQ ID NO 105
<211> LENGTH: 25
<212> TYPE: DNA
<213> ORGANISM: Artificial
<220> FEATURE:
<223> OTHER INFORMATION: Synthetic oligonucleotide

<400> SEQUENCE: 105
cctgcatctt ttatgtgtcc tggaa                                             25

<210> SEQ ID NO 106
<211> LENGTH: 18
<212> TYPE: DNA
<213> ORGANISM: Artificial
<220> FEATURE:
<223> OTHER INFORMATION: Synthetic oligonucleotide

<400> SEQUENCE: 106
catgccttcc ttggagta                                                          18

<210> SEQ ID NO 107
<211> LENGTH: 17
<212> TYPE: DNA
<213> ORGANISM: Artificial
<220> FEATURE:
<223> OTHER INFORMATION: Synthetic oligonucleotide

<400> SEQUENCE: 107
atgccttcct tgaagta                                                           17

<210> SEQ ID NO 108
<211> LENGTH: 16
<212> TYPE: DNA
<213> ORGANISM: Artificial
<220> FEATURE:
<223> OTHER INFORMATION: Synthetic oligonucleotide

<400> SEQUENCE: 108
atggcgccgg atggat                                                            16

<210> SEQ ID NO 109
<211> LENGTH: 19
<212> TYPE: DNA
<213> ORGANISM: Artificial
<220> FEATURE:
<223> OTHER INFORMATION: Synthetic oligonucleotide

<400> SEQUENCE: 109
ctcgatcccg ctccactag                                                         19

<210> SEQ ID NO 110
<211> LENGTH: 13
<212> TYPE: DNA
<213> ORGANISM: Artificial
<220> FEATURE:
<223> OTHER INFORMATION: Synthetic oligonucleotide

<400> SEQUENCE: 110
ccaggcggtt cag                                                               13

<210> SEQ ID NO 111
<211> LENGTH: 13
<212> TYPE: DNA
<213> ORGANISM: Artificial
<220> FEATURE:
<223> OTHER INFORMATION: Synthetic oligonucleotide

<400> SEQUENCE: 111
ccaggaggtt cag                                                               13

<210> SEQ ID NO 112
<211> LENGTH: 21
<212> TYPE: DNA
<213> ORGANISM: Artificial
<220> FEATURE:
<223> OTHER INFORMATION: Synthetic oligonucleotide

<400> SEQUENCE: 112
cagggatgag ggtctgagtt g                                                      21

<210> SEQ ID NO 113

```
<211> LENGTH: 22
<212> TYPE: DNA
<213> ORGANISM: Artificial
<220> FEATURE:
<223> OTHER INFORMATION: Synthetic oligonucleotide

<400> SEQUENCE: 113
ctcttccagg gctaaagttg ct                                              22

<210> SEQ ID NO 114
<211> LENGTH: 16
<212> TYPE: DNA
<213> ORGANISM: Artificial
<220> FEATURE:
<223> OTHER INFORMATION: Synthetic oligonucleotide

<400> SEQUENCE: 114
ctgatgggcc cgccag                                                     16

<210> SEQ ID NO 115
<211> LENGTH: 16
<212> TYPE: DNA
<213> ORGANISM: Artificial
<220> FEATURE:
<223> OTHER INFORMATION: Synthetic oligonucleotide

<400> SEQUENCE: 115
ctgatgggcc caccag                                                     16

<210> SEQ ID NO 116
<211> LENGTH: 26
<212> TYPE: DNA
<213> ORGANISM: Artificial
<220> FEATURE:
<223> OTHER INFORMATION: Synthetic oligonucleotide

<400> SEQUENCE: 116
ccacttaaaa aacaaagggc caagta                                          26

<210> SEQ ID NO 117
<211> LENGTH: 26
<212> TYPE: DNA
<213> ORGANISM: Artificial
<220> FEATURE:
<223> OTHER INFORMATION: Synthetic oligonucleotide

<400> SEQUENCE: 117
agttgtctag agacttgggt ttcaga                                          26

<210> SEQ ID NO 118
<211> LENGTH: 14
<212> TYPE: DNA
<213> ORGANISM: Artificial
<220> FEATURE:
<223> OTHER INFORMATION: Synthetic oligonucleotide

<400> SEQUENCE: 118
cctagagcaa cttc                                                       14

<210> SEQ ID NO 119
<211> LENGTH: 15
<212> TYPE: DNA
<213> ORGANISM: Artificial
<220> FEATURE:
<223> OTHER INFORMATION: Synthetic oligonucleotide

<400> SEQUENCE: 119
```
acctatagca acttc                                                15

<210> SEQ ID NO 120
<211> LENGTH: 24
<212> TYPE: DNA
<213> ORGANISM: Artificial
<220> FEATURE:
<223> OTHER INFORMATION: Synthetic oligonucleotide

<400> SEQUENCE: 120
ccacaggcaa gaattccaaa tgac                                      24

<210> SEQ ID NO 121
<211> LENGTH: 20
<212> TYPE: DNA
<213> ORGANISM: Artificial
<220> FEATURE:
<223> OTHER INFORMATION: Synthetic oligonucleotide

<400> SEQUENCE: 121
gctgcctgac catcaacact                                           20

<210> SEQ ID NO 122
<211> LENGTH: 18
<212> TYPE: DNA
<213> ORGANISM: Artificial
<220> FEATURE:
<223> OTHER INFORMATION: Synthetic oligonucleotide

<400> SEQUENCE: 122
ttctatccat ggaagcaa                                             18

<210> SEQ ID NO 123
<211> LENGTH: 14
<212> TYPE: DNA
<213> ORGANISM: Artificial
<220> FEATURE:
<223> OTHER INFORMATION: Synthetic oligonucleotide

<400> SEQUENCE: 123
atccgtggaa gcaa                                                 14

<210> SEQ ID NO 124
<211> LENGTH: 259
<212> TYPE: DNA
<213> ORGANISM: Homo sapiens
<220> FEATURE:
<221> NAME/KEY: variation
<222> LOCATION: (189)..(189)
<223> OTHER INFORMATION: w is t or a

<400> SEQUENCE: 124
aattctcctc gatggaaacc tgaattactt tcagtttggg gctattatgg ataatgctgc    60
tgtgaatatt cttatataag tgtttttgtg gacacgtttt aattttttctt gagtcaatac  120 ttaggagtgg aattcctagg ttcttttccc agagaggcta tactatttta cacgcctacc   180
aagaaagawt aagaaacaca gttgctccac atttgttgtg gtgttttttgt ttgttttttg   240 cagggtcaca ctttgtcac                                                259

<210> SEQ ID NO 125
<211> LENGTH: 239
<212> TYPE: DNA
<213> ORGANISM: Homo sapiens
<220> FEATURE:

<221> NAME/KEY: variation
<222> LOCATION: (71)..(71)
<223> OTHER INFORMATION: r is a or g

<400> SEQUENCE: 125

```
ctgagttcaa gccattctcc tacctcagcc tcccaagtag ctgggattac aggtgtgtgc    60
cgccacgccc rgctaatttt tgtattttta gtagatatgg gggtttcacc atgttggcca   120
ggctggtttt gaactcctga catcaggtga tctgtccgtc ttgtcctccc aaagtgctgg   180
gattacaggc gtgagccacc gcatccagcc tgttctgtat tctttaatgg aatatgtca   239
```

<210> SEQ ID NO 126
<211> LENGTH: 250
<212> TYPE: DNA
<213> ORGANISM: Homo sapiens
<220> FEATURE:
<221> NAME/KEY: variation
<222> LOCATION: (131)..(131)
<223> OTHER INFORMATION: y is c or t

<400> SEQUENCE: 126

```
aaaccacaat ctggatatta gacatgcttt ttctactggc ttggtcattg tttctaagcc    60
ttttgcatcc tccactggat tgtttacgat agggactggg tacttttctc tctgaagact   120
caatacctgg ygttgactcc tttctctatt acaactattc agggcaacag aaaagacaag   180
gagagcattc ttagctacag ggtgcctaca ttattccaat actgggtcta cgtgtccatg   240
cactatgaga                                                          250
```

<210> SEQ ID NO 127
<211> LENGTH: 245
<212> TYPE: DNA
<213> ORGANISM: Homo sapiens
<220> FEATURE:
<221> NAME/KEY: variation
<222> LOCATION: (17)..(17)
<223> OTHER INFORMATION: r is a or g
<220> FEATURE:
<221> NAME/KEY: variation
<222> LOCATION: (20)..(20)
<223> OTHER INFORMATION: r is a or g
<220> FEATURE:
<221> NAME/KEY: variation
<222> LOCATION: (95)..(95)
<223> OTHER INFORMATION: y is c or t

<400> SEQUENCE: 127

```
gggcttgcag tgagccraga tcrtgccact gcactctagc ctgggcgaaa gagcaagact    60
ccgtctcaaa aaacaaaac aaaacaaaac aaaaycaact ttttttttt tttttttttt    120
aaagaagtga ggtctctctg tgttgcccag gctggagtac agtggcagga tcatagctca   180
ctgcagcctc gaactcctgg ccacaagtga tcctcccacc ttagcctctc aaaatactgt   240
gatta                                                              245
```

<210> SEQ ID NO 128
<211> LENGTH: 238
<212> TYPE: DNA
<213> ORGANISM: Homo sapiens
<220> FEATURE:
<221> NAME/KEY: variation
<222> LOCATION: (160)..(160)
<223> OTHER INFORMATION: r is a or g

<400> SEQUENCE: 128

```
cactcgttag agaggtgcag aaccactgaa gcccagcccg tccccagaga ctcttgtttt    60
```

```
taaccactaa gccaagcttc atggaggagc tggtatctga actggactct gaaatttgca    120
taggactggg acattcagag gaggaagaaa gggggctatr gcagaggaaa cagcatcagc    180
aaaagctcct gaggtagaaa accttcagct gggcttagga catgttggga ggttcagt     238
```

<210> SEQ ID NO 129
<211> LENGTH: 249
<212> TYPE: DNA
<213> ORGANISM: Homo sapiens
<220> FEATURE:
<221> NAME/KEY: variation
<222> LOCATION: (46)..(46)
<223> OTHER INFORMATION: s is g or c
<220> FEATURE:
<221> NAME/KEY: variation
<222> LOCATION: (249)..(249)
<223> OTHER INFORMATION: y is c or t

<400> SEQUENCE: 129

```
ctcctgacct caggcaaacc gcccacctca gcctcctaaa gtgctsggat tacaggtgtg    60
agccactggc acacatcccc acccacccaa tttactttgt tttcaagaaa ccaatttact    120
ttgttttctc aggtaaatta tttactctct tccttttttct ctctgtaggc tagtaagact   180
ccaatcaaag ttgatacatt gtatttacat ctcctctacc ctaaggtgga aaaaggataa    240 acggagtty                                                           249
```

<210> SEQ ID NO 130
<211> LENGTH: 231
<212> TYPE: DNA
<213> ORGANISM: Homo sapiens
<220> FEATURE:
<221> NAME/KEY: variation
<222> LOCATION: (169)..(169)
<223> OTHER INFORMATION: s is g or c

<400> SEQUENCE: 130

```
ctgaggcagg tgaatcacga ggtcaagaga tggagaccat ccagaccaac gtggtgaaac    60
tccgtctcta ctaaaaatac aaaaaattag ctgggcgtgg tggcacgtgc ctgtagtccc    120
agctactcag gaggctgagg caggagaatc gcttgaaacc ggaaggcgsa ggttgcagtg    180
agctgagatt gcgccactgc agtccagcct ggcgacaggg caagactccg t            231
```

<210> SEQ ID NO 131
<211> LENGTH: 267
<212> TYPE: DNA
<213> ORGANISM: Homo sapiens
<220> FEATURE:
<221> NAME/KEY: variation
<222> LOCATION: (252)..(252)
<223> OTHER INFORMATION: k is t or g

<400> SEQUENCE: 131

```
ctcaaaaaaa aaaaaaaaa ttataaacaa ctttatataa gtaaatatga agggataaac    60
tcctaggaaa atattactta gttaagaaat tataaaaaca aaatcaccct agaaccatta    120
aagacattga gtctgtggtc aaaaataaga ttgcaaagaa aacacacctg cgagcccagg    180
tggcttcatc accaagttct atcatacatt caagggacaa agaagggaa actaaaatgg     240 atggtggaag akgatgatat gggtatt                                        267
```

<210> SEQ ID NO 132
<211> LENGTH: 272
<212> TYPE: DNA

<213> ORGANISM: Homo sapiens
<220> FEATURE:
<221> NAME/KEY: variation
<222> LOCATION: (203)..(203)
<223> OTHER INFORMATION: m is c or a

<400> SEQUENCE: 132

```
ccrataacat aaaaaataga ttaatatgta ttttgtatca ttatctatta tatactgtat      60
tcttacaaca cagtaagcta gagaaaatgt taagaaaatc acagagagaa aaagcattga     120
cagtactata ccgtatttat ttagattcta agtttaggtt gtctgtttac aagattagtc     180
gtgtctgaaa tcagagcaac tamagctgca gacctcaatc tatagtacat atcaagaatt     240
caactttttc ctttaatgtc atgactttte tc                                   272
```

<210> SEQ ID NO 133
<211> LENGTH: 252
<212> TYPE: DNA
<213> ORGANISM: Homo sapiens
<220> FEATURE:
<221> NAME/KEY: variation
<222> LOCATION: (233)..(233)
<223> OTHER INFORMATION: y is c or t

<400> SEQUENCE: 133

```
ggaactgcag tatacacaat agccagcaga tgtcagaatg gaatctctta agactcaagt      60
atgaaaacac aataaataac aggagtttct ggaaggactg aggctttctt gctcttctgt     120
gcacaacaca cttcagtcac actggtcttt cttcctcaaa tacatctgct ttaacacttt     180
ttcaaagatg ccccgctcta tctggccaat tcctattcac ccaaacctta ctytatgtgt     240
ctcttcctaa gg                                                         252
```

<210> SEQ ID NO 134
<211> LENGTH: 272
<212> TYPE: DNA
<213> ORGANISM: Homo sapiens

<400> SEQUENCE: 134

```
atatacactt acatacccat aaaaaataat aaaattattt taaaacctac aaaatttgag      60
aaataaagat acaagtttca agtttaaata ggttcaccaa gtgcccacac cacagtgtat     120
taaaataaac acacactaaa tgatgtcatc atggaatata agcatactag gaacaaagat     180
ccttgtttct caggaagaaa tacttagtcc cacaaaaaaa tcaggaatca gaatgatttc     240
agatttctca gcagcaacac tgaaagctag ag                                   272
```

<210> SEQ ID NO 135
<211> LENGTH: 247
<212> TYPE: DNA
<213> ORGANISM: Homo sapiens
<220> FEATURE:
<221> NAME/KEY: variation
<222> LOCATION: (24)..(24)
<223> OTHER INFORMATION: r is a or g

<400> SEQUENCE: 135

```
gctttgcttt aaaattctga aggraaatga ttgctaatct agaaccctat attcatcaaa      60
ctatagaata aagacatttt taaggccagg cacagtggct catgcctata atcccagcac     120
tttgggaggc tgaggtgggc agattacctg aggtcaggag ttcgagacca gcctggccaa     180
catggcaaaa ccctgtctct actaaaaata caaaaattag ccaggcgtgg tggcacgtgc     240
ctgtaat                                                               247
```

<210> SEQ ID NO 136
<211> LENGTH: 243
<212> TYPE: DNA
<213> ORGANISM: Homo sapiens
<220> FEATURE:
<221> NAME/KEY: variation
<222> LOCATION: (119)..(119)
<223> OTHER INFORMATION: r is a or g

<400> SEQUENCE: 136
cagcctcctg aatagttggg actataggca catgccacta tgcctggcta attttttgtat    60 tttttttaaaa gacgaggtat caccatgttg ccaaggctgg tcttgaactc ctgagctcra   120
acaatctgcc cgcctcagcc ccgcaaagtg ctggaattac aggcatgagc cactgcgccc   180
agctcaattt cttaatatta aactgaagac actgagatct gtcagaagct gataaagtca   240
gca                                                                  243

<210> SEQ ID NO 137
<211> LENGTH: 223
<212> TYPE: DNA
<213> ORGANISM: Homo sapiens
<220> FEATURE:
<221> NAME/KEY: variation
<222> LOCATION: (32)..(32)
<223> OTHER INFORMATION: w is t or a

<400> SEQUENCE: 137
aaagtgctgg gtgggattac aggtgtgagc cwacgcgccc ggcagctcaa acattcttca    60
agctgggaga accaggatga ttaaacacgc gcgccggcca ccacgtgcac ttcagtgccc   120
ggaccctgac ccgcagacct caaaccgcgc atatgcccgt cgccttcaac gcgcaccctc   180
cttgctcccc gctaccgttc agctcagttc gaaggccccg atg                     223

<210> SEQ ID NO 138
<211> LENGTH: 200
<212> TYPE: DNA
<213> ORGANISM: Homo sapiens
<220> FEATURE:
<221> NAME/KEY: variation
<222> LOCATION: (85)..(85)
<223> OTHER INFORMATION: k is t or g
<220> FEATURE:
<221> NAME/KEY: variation
<222> LOCATION: (165)..(165)
<223> OTHER INFORMATION: y is c or t

<400> SEQUENCE: 138
ttctggtggc cctgagttct aaattttaaa gccaaagaga ggttggtgta taaagcacct    60
cttgctaaat agcgttttct tctgkcacca ccacgctgaa tatgcacaaa actcttttct   120
tttccctctt agcttggctg gaaatataaa actaaaattt acttyaaaat taatagaaaa   180
caaaaaagat tccctttaaa                                               200

<210> SEQ ID NO 139
<211> LENGTH: 268
<212> TYPE: DNA
<213> ORGANISM: Homo sapiens
<220> FEATURE:
<221> NAME/KEY: variation
<222> LOCATION: (21)..(21)
<223> OTHER INFORMATION: y is c or t

<400> SEQUENCE: 139

```
aggtctgtga ttgtatgtga ycttagtcat ctatttgtta cacaagcatt tttggattgt    60
ttgaaccatt caacacctct ttcctttgca tataaatgga gattaggagg attcttaata   120
ggtagttatt gagcatcaag cctgtcatag atattaagga gaattacagg gtcggggatt   180
tatagtcaaa attcaaagag atgtgaaaat aatgagaaac ctcatggttt aggttttgat   240
gttagaagct cgctgcttca aagatcta                                      268
```

<210> SEQ ID NO 140
<211> LENGTH: 251
<212> TYPE: DNA
<213> ORGANISM: Homo sapiens
<220> FEATURE:
<221> NAME/KEY: variation
<222> LOCATION: (169)..(169)
<223> OTHER INFORMATION: m is c or a

<400> SEQUENCE: 140

```
aagtttaaaa tgtctaaaac ttggctccta atattcccctt ctcgttcctc tgcccccaag    60
aaacttcctc cccttcagtt ttcctcatct caggtagcgg caagtccagc cttcaggttg   120
ctgaggccca aaaccttgga gtcatctttg actcatctct ttctctcama ccctgcatcc   180
aatctggtca gcaaatcctg ttgctgcacc ttcataaagc atatccagaa tcagagtact   240
tctcactcct c                                                        251
```

<210> SEQ ID NO 141
<211> LENGTH: 200
<212> TYPE: DNA
<213> ORGANISM: Homo sapiens
<220> FEATURE:
<221> NAME/KEY: variation
<222> LOCATION: (88)..(88)
<223> OTHER INFORMATION: y is c or t
<220> FEATURE:
<221> NAME/KEY: variation
<222> LOCATION: (119)..(119)
<223> OTHER INFORMATION: k is t or g

<400> SEQUENCE: 141

```
tttggaaaca tttttgacat accttagtgc acagagctta atgcagagct tggcatacag    60
taagccttca atgtctatct tctgtatyct ttttttcccct ttactcctka tcttagaatg   120
tgcagcattt cacagatctg gttataatga cattggaccct aaagtgattc tctcagccta   180
ggagagaggc cagtggcgat                                               200
```

<210> SEQ ID NO 142
<211> LENGTH: 200
<212> TYPE: DNA
<213> ORGANISM: Homo sapiens
<220> FEATURE:
<221> NAME/KEY: variation
<222> LOCATION: (75)..(75)
<223> OTHER INFORMATION: y is c or t

<400> SEQUENCE: 142

```
aagtattttta aaggatttga gttcactgga gagatgtcct gttttttaagt gactacgaga    60 acctggtcac tgttyccaat atcagaagga ctgccacggg gcagaggatg aggagttgtc   120
cttcatgggt ccagagggca gaactaggac cagtagggag gtagatgtta acctgagaat   180
gggaagaact ttaatggcta                                               200
```

<210> SEQ ID NO 143
<211> LENGTH: 200

```
<212> TYPE: DNA
<213> ORGANISM: Homo sapiens

<400> SEQUENCE: 143
aaggcaaggt gattttcat tttcaaaaat aatttattga ttaattacct accatgtgca    60
ggacattgtc ctaagtgcta gaggagccca aatgtgaact aggcaagtag tgtgctccta   120
gagagctcct ggtgtaagag ggaagataaa agtcatctat ccatgcatcc attcactcag   180
tgaatatata ctgagcacct                                               200

<210> SEQ ID NO 144
<211> LENGTH: 152
<212> TYPE: DNA
<213> ORGANISM: Homo sapiens
<220> FEATURE:
<221> NAME/KEY: variation
<222> LOCATION: (146)..(146)
<223> OTHER INFORMATION: r is a or g

<400> SEQUENCE: 144
ctgtttcttt aaggtgactt agcaaatctc tactctaata cattatgtgt tgatgtccta    60
ttttaactct caaggacaat ctcatttcta attctttcag gatcactcac tgttgccctt   120
agtactgaca cactttaca gcctcragat tt                                  152

<210> SEQ ID NO 145
<211> LENGTH: 169
<212> TYPE: DNA
<213> ORGANISM: Homo sapiens
<220> FEATURE:
<221> NAME/KEY: variation
<222> LOCATION: (67)..(67)
<223> OTHER INFORMATION: y is c or t

<400> SEQUENCE: 145
aggctcattt tcctcatcta taaaatagga ataaatacca tattcttcac agggctgctg    60
tgagaaytaa ataacatgca ccataaatca cttagtccag caccgggcat agagaaggcc   120
ctaagtaaat ggttgctatt gatcatcatg atttaaaaaa aaaaaaact              169

<210> SEQ ID NO 146
<211> LENGTH: 200
<212> TYPE: DNA
<213> ORGANISM: Homo sapiens
<220> FEATURE:
<221> NAME/KEY: variation
<222> LOCATION: (48)..(48)
<223> OTHER INFORMATION: w is t or a

<400> SEQUENCE: 146
gaagttcgag cagtactggt ttagagtaca cctgctttgc aagtgatwgt aagtgtgtct    60
tcattccctt taatgtaaca gagctccaca cataattgga cttttgtagt cattgccagt   120
tactccacct tcgaggcgat ctttgctgac tcaggttttc ctgcgttttc ccagagctgt   180
ttctttcagc tcccatggtc                                               200

<210> SEQ ID NO 147
<211> LENGTH: 200
<212> TYPE: DNA
<213> ORGANISM: Homo sapiens
<220> FEATURE:
<221> NAME/KEY: variation
<222> LOCATION: (138)..(138)
<223> OTHER INFORMATION: s is g or c
```

```
<400> SEQUENCE: 147
cttatcagaa cctaaccatg cctctctggc tggcggctaa gggaacctgc ctacctgagg        60
gatggccact tgatgtagca tagtgaggag aagggactta ggcctgactt gaccaaaatc       120
ttagtgtgtg atctttcsca agctccttcc tccttccctt cctggtgctg cagcgtcttc       180
cctataaaat gaataatgga                                                   200

<210> SEQ ID NO 148
<211> LENGTH: 200
<212> TYPE: DNA
<213> ORGANISM: Homo sapiens
<220> FEATURE:
<221> NAME/KEY: variation
<222> LOCATION: (23)..(23)
<223> OTHER INFORMATION: s is g or c
<220> FEATURE:
<221> NAME/KEY: variation
<222> LOCATION: (31)..(31)
<223> OTHER INFORMATION: r is a or g

<400> SEQUENCE: 148
actagatgac cgattgtagg casgccaatt rcatgctcag ggcagtagca atgcagggcc        60
acccgccaac atcatttgt ctggaaaaca tttgatacct gatgctttcc taaaaacatt       120
aaagtaatcc tcacaggaaa tatcagaact ttactggacc tctttatact tagtttatag      180
ttcagtgctt tttaaaaaaa                                                   200

<210> SEQ ID NO 149
<211> LENGTH: 233
<212> TYPE: DNA
<213> ORGANISM: Homo sapiens
<220> FEATURE:
<221> NAME/KEY: variation
<222> LOCATION: (11)..(11)
<223> OTHER INFORMATION: m is c or a

<400> SEQUENCE: 149
ctcgtgtccc maagcccggc tcggggggcgc gtccgtgggc tagctcagga cctgccatcg       60
tgaactgttt gcacagtagc gatgtgtgct taagtttccg agatctgcat ggtgtagtga      120
gtggaaacag cggcaacgcg ggaggggggag agacctgggt tcaggtgcgg ccgcggccag      180
cgccaacttt ctgagtgacc tcagaccaac cctctctgtc cgtcctcgat ggc             233

<210> SEQ ID NO 150
<211> LENGTH: 187
<212> TYPE: DNA
<213> ORGANISM: Homo sapiens
<220> FEATURE:
<221> NAME/KEY: variation
<222> LOCATION: (19)..(19)
<223> OTHER INFORMATION: r is a or g

<400> SEQUENCE: 150
gattttattt ccttcctcra catcctggtt ttaagtttct agcattatga aatcagagag        60
ctggtgaggg tgtgcttggt gaccagagca gagttgtggt acctaagttt gtctttcctg      120
aatgagaccc catccttgaa gctaatttgt ccagagcctt ttatctctct gacgcattca      180
aatgcca                                                                187

<210> SEQ ID NO 151
<211> LENGTH: 317
<212> TYPE: DNA
<213> ORGANISM: Homo sapiens
```

```
<220> FEATURE:
<221> NAME/KEY: variation
<222> LOCATION: (269)..(269)
<223> OTHER INFORMATION: y is c or t

<400> SEQUENCE: 151
ttattacaaa gttcttcatt attccaagcc aaaaatcttc ctctcggcaa tggttgcccc      60
attggcccga tcctgtcctt tgaagcccca cacacaaaaa atccatttct tcttccctat     120
gacagctagt taggccactt ggaccttcaa agacagggat caggccccca catcttcact     180
tctttaggca gaatgcccac tttatctggc ccctgaaaa gctaagaatg ggacaccgct      240
gtgcaggtgg gggtctgatc agcccagaya ggagcaagcc cactgcagcc tcacttcgga    300
atctatattt gcgttag                                                   317

<210> SEQ ID NO 152
<211> LENGTH: 200
<212> TYPE: DNA
<213> ORGANISM: Homo sapiens
<220> FEATURE:
<221> NAME/KEY: variation
<222> LOCATION: (30)..(30)
<223> OTHER INFORMATION: y c or t
<220> FEATURE:
<221> NAME/KEY: variation
<222> LOCATION: (78)..(78)
<223> OTHER INFORMATION: r is a or g

<400> SEQUENCE: 152
tgggcaggga ccgagccttg ctgctcatty agtacggagc ccagaaggag gcctgggggg     60
tacagtgttg accgatgraa tgaatgaatg catggctatg actacttcct tagctgcatc    120
tggctcccag ctgccttcat tggtctctac agtcatcagt agtatcctgg ctaagtcaag    180
agcatatgtg ggcctctgtg                                               200

<210> SEQ ID NO 153
<211> LENGTH: 400
<212> TYPE: DNA
<213> ORGANISM: Homo sapiens
<220> FEATURE:
<221> NAME/KEY: variation
<222> LOCATION: (207)..(207)
<223> OTHER INFORMATION: k is t or g

<400> SEQUENCE: 153
gatgcgtaca acctgtgcac actcatccct ctcttgtatt tagtctgccc aatttaattt    60
gtttagatac cgtaggcttt tattgattgc ccattagaag tttagcctag tgttgacagc    120
ctaggggtat aagagacatc attagccaga aatttctttt gtagctggac tagtaagtct    180
tatacccaag agtcagtgaa cagaatkatc tgttcactgg ggattgctga gtaaattggt    240
gtgagtgcca ggatttctgc cccaggctga gagatctgga tagatggatg ctgaagatgg    300
ttcttcagga agtcttttgg aggagtctgc attggagatg ggccaggtgg ggattgcatg    360
ccagagtgga gatgcagggg gagggggctg atcagcaggt                          400

<210> SEQ ID NO 154
<211> LENGTH: 27
<212> TYPE: DNA
<213> ORGANISM: Artificial
<220> FEATURE:
<223> OTHER INFORMATION: Synthetic oligonucleotide

<400> SEQUENCE: 154
```

```
tcaaacattt tagacgagtg ggaaact                                      27
```

<210> SEQ ID NO 155
<211> LENGTH: 25
<212> TYPE: DNA
<213> ORGANISM: Artificial
<220> FEATURE:
<223> OTHER INFORMATION: Synthetic oligonucleotide

<400> SEQUENCE: 155

```
tgagttacct gtcatgggtt ttgtt                                        25
```

<210> SEQ ID NO 156
<211> LENGTH: 20
<212> TYPE: DNA
<213> ORGANISM: Artificial
<220> FEATURE:
<223> OTHER INFORMATION: Synthetic oligonucleotide

<400> SEQUENCE: 156

```
ctcattaccc tctttctttt                                              20
```

<210> SEQ ID NO 157
<211> LENGTH: 19
<212> TYPE: DNA
<213> ORGANISM: Artificial
<220> FEATURE:
<223> OTHER INFORMATION: Synthetic oligonucleotide

<400> SEQUENCE: 157

```
tctctcatta ccctctttt                                               19
```

<210> SEQ ID NO 158
<211> LENGTH: 23
<212> TYPE: DNA
<213> ORGANISM: Artificial
<220> FEATURE:
<223> OTHER INFORMATION: Synthetic oligonucleotide

<400> SEQUENCE: 158

```
tcccatagta tccagcactg aca                                          23
```

<210> SEQ ID NO 159
<211> LENGTH: 29
<212> TYPE: DNA
<213> ORGANISM: Artificial
<220> FEATURE:
<223> OTHER INFORMATION: Synthetic oligonucleotide

<400> SEQUENCE: 159

```
agcctagggt attcattatt gatgagcta                                    29
```

<210> SEQ ID NO 160
<211> LENGTH: 15
<212> TYPE: DNA
<213> ORGANISM: Artificial
<220> FEATURE:
<223> OTHER INFORMATION: Synthetic oligonucleotide

<400> SEQUENCE: 160

```
atctgggaga gaaat                                                   15
```

<210> SEQ ID NO 161
<211> LENGTH: 15
<212> TYPE: DNA
<213> ORGANISM: Artificial

```
<220> FEATURE:
<223> OTHER INFORMATION: Synthetic oligonucleotide

<400> SEQUENCE: 161
atctgggaca gaaat                                                      15

<210> SEQ ID NO 162
<211> LENGTH: 30
<212> TYPE: DNA
<213> ORGANISM: Artificial
<220> FEATURE:
<223> OTHER INFORMATION: Synthetic oligonucleotide

<400> SEQUENCE: 162
gggaaacaaa ccaataataa tggaagacaa                                      30

<210> SEQ ID NO 163
<211> LENGTH: 24
<212> TYPE: DNA
<213> ORGANISM: Artificial
<220> FEATURE:
<223> OTHER INFORMATION: Synthetic oligonucleotide

<400> SEQUENCE: 163
gggagcacat tttgagttgt aagg                                            24

<210> SEQ ID NO 164
<211> LENGTH: 14
<212> TYPE: DNA
<213> ORGANISM: Artificial
<220> FEATURE:
<223> OTHER INFORMATION: Synthetic oligonucleotide

<400> SEQUENCE: 164
agcaggtagc tttt                                                       14

<210> SEQ ID NO 165
<211> LENGTH: 15
<212> TYPE: DNA
<213> ORGANISM: Artificial
<220> FEATURE:
<223> OTHER INFORMATION: Synthetic oligonucleotide

<400> SEQUENCE: 165
cagcagatag ctttt                                                      15

<210> SEQ ID NO 166
<211> LENGTH: 25
<212> TYPE: DNA
<213> ORGANISM: Artificial
<220> FEATURE:
<223> OTHER INFORMATION: Synthetic oligonucleotide

<400> SEQUENCE: 166
ggactgggta cttttctctc tgaag                                           25

<210> SEQ ID NO 167
<211> LENGTH: 24
<212> TYPE: DNA
<213> ORGANISM: Artificial
<220> FEATURE:
<223> OTHER INFORMATION: Synthetic oligonucleotide

<400> SEQUENCE: 167
cttgtctttt ctgttgccct gaat                                            24
```

<210> SEQ ID NO 168
<211> LENGTH: 17
<212> TYPE: DNA
<213> ORGANISM: Artificial
<220> FEATURE:
<223> OTHER INFORMATION: Synthetic oligonucleotide

<400> SEQUENCE: 168
agtcaacacc aggtatt                                                17

<210> SEQ ID NO 169
<211> LENGTH: 14
<212> TYPE: DNA
<213> ORGANISM: Artificial
<220> FEATURE:
<223> OTHER INFORMATION: Synthetic oligonucleotide

<400> SEQUENCE: 169
caacgccagg tatt                                                   14

<210> SEQ ID NO 170
<211> LENGTH: 22
<212> TYPE: DNA
<213> ORGANISM: Artificial
<220> FEATURE:
<223> OTHER INFORMATION: Synthetic oligonucleotide

<400> SEQUENCE: 170
gggccacgta gatgagaaag tt                                          22

<210> SEQ ID NO 171
<211> LENGTH: 19
<212> TYPE: DNA
<213> ORGANISM: Artificial
<220> FEATURE:
<223> OTHER INFORMATION: Synthetic oligonucleotide

<400> SEQUENCE: 171
ggaagatgcg cgaggatgt                                              19

<210> SEQ ID NO 172
<211> LENGTH: 16
<212> TYPE: DNA
<213> ORGANISM: Artificial
<220> FEATURE:
<223> OTHER INFORMATION: Synthetic oligonucleotide

<400> SEQUENCE: 172
ccgtatggag gagatc                                                 16

<210> SEQ ID NO 173
<211> LENGTH: 15
<212> TYPE: DNA
<213> ORGANISM: Artificial
<220> FEATURE:
<223> OTHER INFORMATION: Synthetic oligonucleotide

<400> SEQUENCE: 173
cgtatggaag agatc                                                  15

<210> SEQ ID NO 174
<211> LENGTH: 16
<212> TYPE: DNA
<213> ORGANISM: Artificial
<220> FEATURE:
<223> OTHER INFORMATION: Synthetic oligonucleotide

<400> SEQUENCE: 174
tgggcttccc gaccac                                                      16

<210> SEQ ID NO 175
<211> LENGTH: 15
<212> TYPE: DNA
<213> ORGANISM: Artificial
<220> FEATURE:
<223> OTHER INFORMATION: Synthetic oligonucleotide

<400> SEQUENCE: 175
ccggtgcccc tcctg                                                       15

<210> SEQ ID NO 176
<211> LENGTH: 20
<212> TYPE: DNA
<213> ORGANISM: Artificial
<220> FEATURE:
<223> OTHER INFORMATION: Synthetic oligonucleotide

<400> SEQUENCE: 176
cagatacagc ttttatgcgc                                                  20

<210> SEQ ID NO 177
<211> LENGTH: 19
<212> TYPE: DNA
<213> ORGANISM: Artificial
<220> FEATURE:
<223> OTHER INFORMATION: Synthetic oligonucleotide

<400> SEQUENCE: 177
agatacagct tttctgcgc                                                   19

<210> SEQ ID NO 178
<211> LENGTH: 25
<212> TYPE: DNA
<213> ORGANISM: Artificial
<220> FEATURE:
<223> OTHER INFORMATION: Synthetic oligonucleotide

<400> SEQUENCE: 178
catctcctct accctaaggt ggaaa                                            25

<210> SEQ ID NO 179
<211> LENGTH: 22
<212> TYPE: DNA
<213> ORGANISM: Artificial
<220> FEATURE:
<223> OTHER INFORMATION: Synthetic oligonucleotide

<400> SEQUENCE: 179
cgaccttaga ccacgtgaac tc                                               22

<210> SEQ ID NO 180
<211> LENGTH: 14
<212> TYPE: DNA
<213> ORGANISM: Artificial
<220> FEATURE:
<223> OTHER INFORMATION: Synthetic oligonucleotide

<400> SEQUENCE: 180
accacatgaa ctcc                                                        14

<210> SEQ ID NO 181

-continued

```
<211> LENGTH: 14
<212> TYPE: DNA
<213> ORGANISM: Artificial
<220> FEATURE:
<223> OTHER INFORMATION: Synthetic oligonucleotide

<400> SEQUENCE: 181
accacataaa ctcc                                                    14

<210> SEQ ID NO 182
<211> LENGTH: 18
<212> TYPE: DNA
<213> ORGANISM: Artificial
<220> FEATURE:
<223> OTHER INFORMATION: Synthetic oligonucleotide

<400> SEQUENCE: 182
ccttcggagg ccttggat                                                18

<210> SEQ ID NO 183
<211> LENGTH: 26
<212> TYPE: DNA
<213> ORGANISM: Artificial
<220> FEATURE:
<223> OTHER INFORMATION: Synthetic oligonucleotide

<400> SEQUENCE: 183
ctttgtgagg agaaaagcaa cattca                                       26

<210> SEQ ID NO 184
<211> LENGTH: 15
<212> TYPE: DNA
<213> ORGANISM: Artificial
<220> FEATURE:
<223> OTHER INFORMATION: Synthetic oligonucleotide

<400> SEQUENCE: 184
ctgcctctga ttatt                                                   15

<210> SEQ ID NO 185
<211> LENGTH: 16
<212> TYPE: DNA
<213> ORGANISM: Artificial
<220> FEATURE:
<223> OTHER INFORMATION: Synthetic oligonucleotide

<400> SEQUENCE: 185
tctgcctcta attatt                                                  16
```

METHOD OF ANALYZING BREAST CANCER SUSCEPTIBILITY AND RESISTANCE

CROSS-REFERENCE TO RELATED APPLICATION

This application claims the benefit of U.S. 60/739,798, filed Nov. 23, 2005 and 60/661,420, filed Mar. 14, 2005. Both provisional applications are incorporated by reference herein as if fully set forth below.

STATEMENT REGARDING FEDERALLY SPONSORED RESEARCH OR DEVELOPMENT

The invention was made with United States government support awarded by the following agency: NIH Grants: CA77494 and CA28954. The United States has certain rights in this invention.

BACKGROUND OF THE INVENTION

Despite immense efforts, the search for modifier genes underlying complex diseases has not been highly productive. Alleles of modifier genes that influence disease risk have a moderate to high population frequency with a low penetrance. It has been suggested that alleles acting in this manner comprise the majority of genetic risk for many common diseases, such as breast cancer (D. E. Reich and E. S. Lander, *Trends Genetics* 17, 502 (2001), B. A. Ponder, *Nature* 411, 336 (2001)). It is estimated that if most risk alleles are identified, it would be possible to assign ~90% of breast cancer risk to 50% of women (P. D. P. Pharoah et al., *Nature Genet.* 31, 33 (2002)). In most studies, candidate modifier genes are selected based on their function, such as DNA repair or estrogen metabolism for breast cancer, and thus are classified as biased. Over 100 biased candidate modifier genes have been tested in breast cancer case-control association studies (>400 SNPs); few, if any, show a consistent and significant association with risk in large sample populations (P. D. P. Pharoah, A. M. Dunning, B. A. J. Ponder, D. F. Easton, *Nature* 4, 850 (2004)). This suggests the need for an unbiased strategy to identify breast cancer modifier genes.

Previously, our laboratory has pursued the identification of unbiased candidate loci by using whole genome linkage studies in inbred-rat mammary cancer models followed by fine-mapping in congenic rats. Polymorphisms in human genomic regions orthologous to these rat loci can be subsequently tested for association with breast cancer risk in large case-control population-based studies. In this application we present an example that supports this unbiased approach.

Using a backcross of [Wistar-Kyoto (WKy)×Wistar-Furth (WF)]$F_1$×WF rats, we previously identified four mammary carcinoma susceptibility QTL, Mcs5, Mcs6, Mcs7, and Mcs8, on rat chromosomes 5, 7, 10, and 14, respectively (H. Lan et al., *Genetics* 157, 331 (2001)). The WKy allele of Mcs5 acts to suppress mammary tumor multiplicity in a susceptible WF genetic background. To narrow the Mcs5 QTL region, we collected multiple WF.WKy congenic recombinant lines within the Mcs5 locus. Selected lines were phenotyped to determine their susceptibility to 7-12 dimethylbenz(a)anthracene (DMBA)-induced mammary carcinogenesis.

Data from these congenic rat lines containing various WKy genomic intervals of the Mcs5 QTL region identified three Mcs5 subloci. Congenic WKy-homozygous and heterozygous females from a line defining one sublocus, Mcs5a, had the phenotype of resistance to DMBA-induced mammary cancer (D. J. Samuelson, B. A. Aperavich, J. D. Haag, M. N. Gould, *Cancer Res.* 65, 9637 (2005)).

Needed in the art of breast cancer detection and therapy are specific minor alleles that correlate with breast cancer susceptibility or resistance.

BRIEF SUMMARY OF THE INVENTION

In one embodiment, the present invention is a method of analyzing breast cancer susceptibility or resistance, comprising the steps of obtaining a DNA sample from a patient, genotyping the sample for the presence of the minor allele of single nucleotide polymorphisms rs6476643 or rs2182317 or a polymorphism correlating at $r^2>0.7$ with rs6476643 or rs2182317, and correlating the identity of the allele with risk assessment data.

Preferably, the minor allele is a minor allele selected from the group consisting of rs2182317
rs6476643
138-9899
rs10758441
rs7042509
114-117
d3-169
rs12378421
r3-116
rs17505776
rs4878708
rs4878709
rs4878710
rs10973450
l4-70
m4-218
rs4490927
x4-77
z4-66
f5-152
rs4878713
y5-43
i6-31
i6-103

In another embodiment, the present invention is a method of finding minor alleles that correlate to human breast cancer susceptibility or resistance, comprising the steps of sequencing human genomic regions MCS5A1 or MCS5A2, identifying at least one polymorphism, genotyping individuals for the presence or absence of the polymorphism and, determining whether the polymorphism correlates to rs212317 (plus strand allele T) or rs6476643 (plus strand allele T) with the $r^2$ statistic at $r^2>0.7$.

In another embodiment, one determines whether the polymorphism correlates at $r^2>0.7$ to the group consisting of rs2182317
rs6476643
138-9899
rs10758441
rs7042509
114-117
d3-169
rs12378421
r3-116
rs17505776
rs4878708
rs4878709
rs4878710

-continued rs10973450
l4-70
m4-218
rs4490927
x4-77
z4-66
f5-152
rs4878713
y5-43
i6-31
i6-103

In another embodiment, the present invention is a method of treating or preventing breast cancer comprising mimicking the biological effect of MCS5A1 and MCS5A2 alleles that increase/decrease susceptibility to breast cancer.

In another embodiment, the present invention is a method of assaying molecules for their ability to interact with the FBXO10 and FMRPD1 gene loci or the FBXO10 and FMRPD1 gene loci products comprising the steps of exposing a candidate molecule to the FBXO10 and FMRPD1 gene loci or gene loci products and determining whether the candidate molecule has interacted with the loci or the gene products.

Other objects, features and advantages of the present invention will be apparent to one of skill after review of the specification, claims and drawings.

DESCRIPTION OF THE INVENTION

A. In General

Our lab has collected DNA from ~1,500 women in Wisconsin diagnosed with breast cancer and ~1,500 controls. In order to locate genes relevant to human breast cancer risk, our lab has used QTLs (Quantitative Trait Locus) observed in inbred rat strains as a guide for candidate regions in the human genome. We have chosen a sub-locus of the Msc5-QTL that had the highest LOD (Log of the Odds Ratio) score of all QTLs found in our original experiment on which this study is based (Lan, et al., *Genetics* 157:331-339, 2001).

Mcs5a is a sub-locus of the Mcs5-QTL that confers resistance to the development of DMBA-induced mammary carcinomas in rats. The Mcs5a sub-locus has been confirmed in congenic strains. Currently, sufficient recombinant strains have been analyzed to narrow the candidate region to ~116,000 bp. The Mcs5a locus when homozygous, in addition to conferring mammary carcinoma resistance to rats after DMBA treatment, also reduces mammary tumor multiplicity by ~50% as compared to littermates without Mcs5a after NMU treatment and over expression of neu. The rat genes in this region have been assayed for different levels of gene expression between the susceptible and resistant parent strains and all gene exons have been sequenced.

In order to further fine-map the Mcs5a locus, recombinant rat lines were collected and phenotyped for resistance to DMBA-induced mammary carcinogenesis. The results are presented in FIG. 1. Carcinoma development in DMBA-treated WKy-homozygous rats from congenic lines O, WW, and XX was reduced ~50% for each line (FIG. 1).

The current boundaries of the Mcs5a locus are given by the overlapping WKy sequences of congenic recombinant lines WW and XX, which define a genomic interval of ~116 Kb containing Mcs5a. Further analysis of additional congenic recombinant lines within this interval demonstrated that at least two genetic elements exist within Mcs5a. They are defined by incorporating phenotype data from congenic lines LL and B3. These lines have a very short interval of overlap (415 bp) within the Mcs5a locus, and together cover the entire putative Mcs5a locus.

Figure 1:
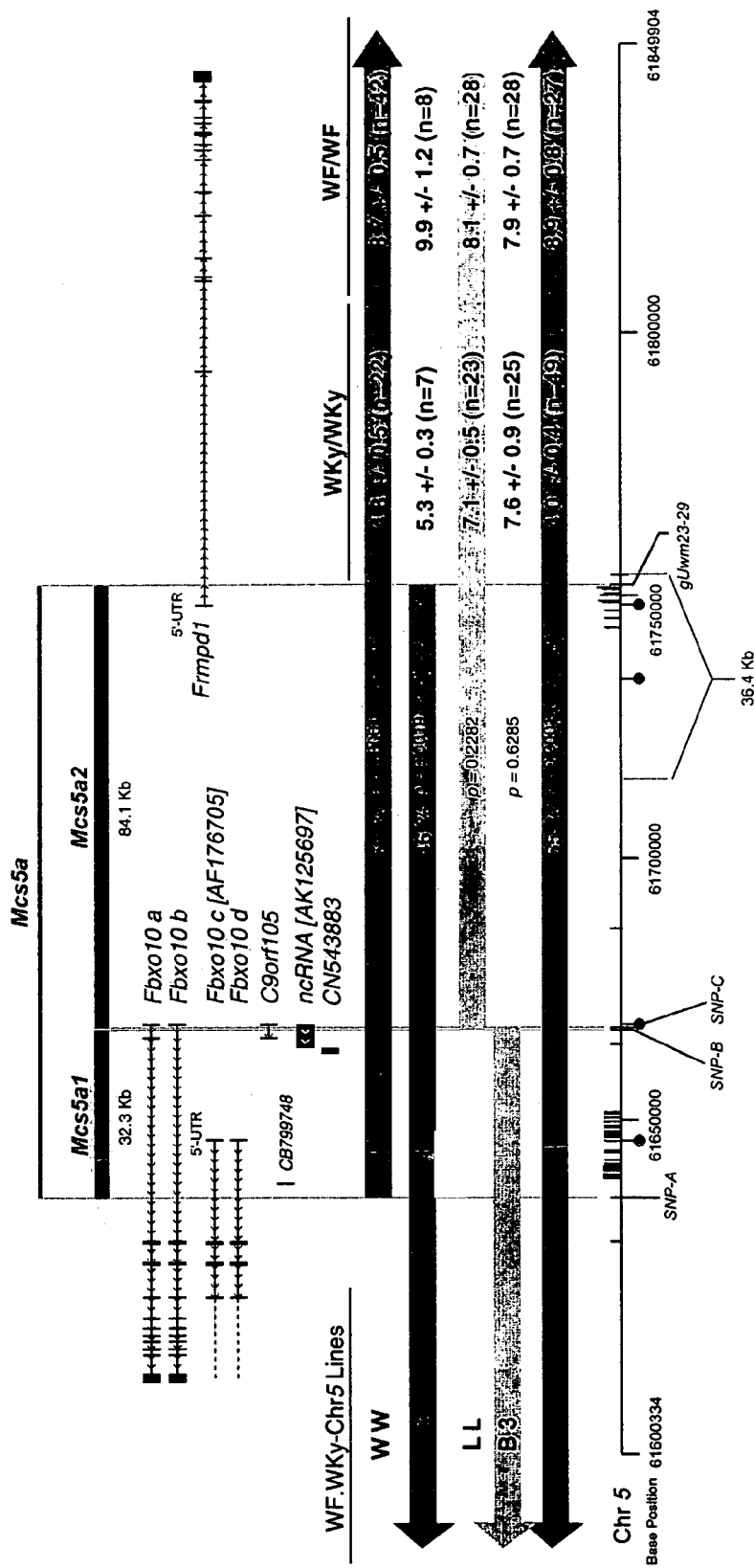
FIG. 1. Positional-mapping of synthetically interacting gene loci within the compound rat QTL, Mcs5a. Mcs5a (~116 Kb) is a compound QTL located on rat chromosome 5. Adjacent Mcs5a1 (32.3 Kb) and Mcs5a2 (84.1 Kb), are synthetically interacting loci within Mcs5a and were identified using recombinant congenic lines. Rat mammary gland transcripts are mapped as exons connected by intronic sequence. Mcs phenotypes of congenic lines (WF.WKy-Chr5), containing different segments of the Mcs5a WKy allele of congenic line 0, were determined in female rats administered DMBA (65 mg/kg) at 50-55 days of age. Tumor multiplicity data presented are average number of mammary carcinomas≧3×3 mm per rat±S.E at 15 wks post-induction. Congenic homozygous (WKy/WKy) females were compared to WF/WF littermates using the nonparametric Mann-Whitney test. Percent reduction in mammary carcinomas/rat compared to Mcs-WF/WF littermates is shown at center for lines determined to be significantly different (P<0.05) than the Mcs-WF/WF rats. The Mcs resistant and Mcs susceptible congenic lines that define Mcs5a are shown by the WKy alleles they contain. The relevant end of the WKy sequence in each congenic line is indicated by a genetic marker and a dashed-vertical line. SNP-A, SNP-B, SNP-C, and gUwm23-29, are on chromosome 5 at base positions: 61,634,906; 61,667,232; 61,667,646; and 61,751,595-61,751,793; respectively. The x-axis represents rat chromosome 5 and the designated marks are SNPs, INDELs, microsatellites, CpG islands, and the UCSC Genome Browser June 2003 rat assembly base position. The 36.4 Kb region marked by brackets contains the human/rat conserved sequence segments (60% identity over 90 bp) that were resequenced.

Interestingly, WKy-homozygous rats from either line LL or B3 do not have a phenotype of resistance (FIG. 1). The simplest hypothesis to explain these data is that Mcs5a is a compound locus containing two genetic elements, termed Mcs5a1 and Mcs5a2, which interact synthetically to confer the Mcs5a mammary cancer resistance phenotype. Mcs5a1 is defined by the overlapping genomic region of congenic lines WW and B3, which is ~32 Kb (~30 Kb in humans). Mcs5a2 is defined by the overlapping genomic regions of congenic lines LL and XX and covers ~84 Kb (~63 Kb in humans).

We localized the human region that is orthologous to the rat Mcs5a locus (Mcs5a1 and 5a2) to ~93 Kb on human chromosome 9 and determined the human haplotype block structure of a 1 Mb region surrounding this area. Haplotypes from a single block (Block 4) in the MCS5A locus were tested for association with breast cancer risk in a Wisconsin case-control study (1,500 cases; 1,405 controls). Haplotype block 4.2, allele 4, that spanned SNPs rs10758440, rs999988, rs2182317, rs2381718, was found to be marginally significant in the Wisconsin population.

These four SNPs were also tested in the larger UK population (4,364 cases; 4,547 control). Table 2 demonstrates a highly significant association of the minor allele of rs2182317 (SNP-3) with a reduction in risk of developing breast cancer. The Wisconsin and UK populations combined (N=11,779 women) yielded a heterozygous odds ratio of 0.86 (0.79-0.94), and a homozygous odds ratio of 0.77 (0.57-1.04). The uncorrected Chi-square trends test, stratified by study, yielded a P value of 0.0003 (Table 2), and when corrected for multiple comparisons using the conservative Bonferroni method the P value was 0.001.

We tested the additional genetic variation that was revealed after resequencing the human regions to determine if a polymorphism within MCS5A1 that was not correlated to SNP-3 in the MCS5A2 region associated independently with breast cancer risk in women. A total of 48 human chromosomes were resequenced at the MCS5A1 locus. Polymorphisms were "binned" into groups of polymorphisms that were highly correlated to each other. Bins were screened for an association with breast cancer risk in the Wisconsin case-control population.

The results identified one bin (rs6476643, rs10758441, rs7042509, and an indel, 138-9899, on chr9:37563886-37563887) that qualified for further testing in the second population. One SNP from this bin (rs6476643, SNP-A1) was evaluated further in the UK breast cancer case-control population. The combined results for SNP-A1 yielded an odds ratio of 1.05 (0.97-1.13) for heterozygotes and 1.19 (1.03-1.38) for minor allele homozygotes (Table 2). A trends test, stratified by study, was significant for the minor allele (P=0.022).

The SNP bin that includes rs6476643 (SNP-A1) contains 4 polymorphisms with similar minor allele distributions but slightly different minor allele frequencies. The SNP bin including rs6476643 is close to an area of recombination and spans ~6 Kb. No polymorphisms correlated to this bin were found outside of this 6 Kb MCS5A1 region. This result is based on the distribution of the minor alleles found in the resequencing effort.

SNP-3 (rs2182317) and other polymorphisms listed in the bin are candidates for the causative SNP(s) in MCS5A2. These candidates include many highly correlated SNPs. Any one, or combination of SNPs found exclusively, or mostly, in individuals carrying the minor allele fo rs2182317 may be the causative SNP. We hypothesize that the causative SNP is in or near a conserved region; thus, the genetic variation found in this study may effectively narrow the region containing the causative SNP.

Considering all SNPs that are more rare or more common than rs2182317 and found in carriers of the minor allele of this SNP, the possible candidate SNPs include: 114-117 (MAF=~0.02-0.04), d3-169, rs12378421, r3-116, rs17505776, rs4878708, rs4878709, rs4878710, rs10973450, l4-70, m4-218, rs4490927, x4-77, z4-66, f5-152, rs4878713, y543, i6-31, and i6-103. Testing these SNP-3 correlated SNPs individually will not, by itself, distinguish one of these SNPs as the causative SNP in MCS5A2. This is because all but one of these SNPs, 114-117, has an identical or very similar minor allele frequency and distribution to rs2182317.

Table 1, below, summarizes our risk assessment data.

TABLE 1

| MCS5A1-Minor Alleles that Increase Risk of Breast Cancer | |
|---|---|
| Polymorphism | Minor Allele Associated with risk on the (+) strand |
| rs6476643 | T |
| 138-9899 | * (deletion) |
| rs10758441 | T |
| rs7042509 | G |

Sequences not found in NCBI database:

138-9899
Indel 37563886^37563887
AAAATCTTAATCAAATGTCTCTTTGTGTACATTCCTTTATGTATACAGTA
TCAAACATTTTAGACGAGTGGGAAACTAATAATCACTAAACTAAAAGA[A
AGA]GGGTAATGAGAGAAATTAGCAGACATTTCAAACAAAACCCATGACA
GGTAACTCAAGAATAGGTTTCATTCATTAAGGCAAACTGAAAGAACAAAA
CACTTGTTCCATCTATTTCCTGACTGAAGCAGGTACAAGGAATTTGTTTA
CTTCACATCTTCCTGTGAAAAG

| MCS5A2-Minor Alleles that Decrease Risk of Breast Cancer | |
|---|---|
| Polymorphism | Minor Allele Associated with risk on the (+) strand |
| rs2182317 | T |
| 114-117 (SEQ ID NO: 2) | T |
| d3-169 (SEQ ID NO: 3) | A |
| rs12378421 | G |
| r3-116 (SEQ ID NO: 4) | T |
| rs17505776 | C |
| rs4878708 | A |
| rs4878709 | A |
| rs4878710 | A |
| rs10973450 | C |
| l4-70 (SEQ ID NO: 5) | T |
| m4-218 (SEQ ID NO: 6) | G |
| rs4490927 | T |
| x4-77 (SEQ ID NO: 7) | A |
| z4-66 (SEQ ID NO: 8) | G |
| f5-152 (SEQ ID NO: 9) | G |
| rs4878713 | G |

TABLE 1-continued

| | |
|---|---|
| y5-43 (SEQ ID NO: 10) | C |
| i6-31 (SEQ ID NO: 11) | T |
| i6-103 (SEQ ID NO: 12) | G |

Sequences not in the NCBI database:

114-117
Chr9: 37610247
AAAAACACAAAAACCAAAGGCTTCCAGATGAGGACAGAATTCCATTTTAC
CCTTCACTTCTACACAAATAGGCAAAATTAGAAGTGGAACACTCGTGTTT
ATCTGCCTCCAGGTCAYAGCATCACAGCAGAGTAGAAGGAGCAGTGGCTT
GGCATTGCTGAGAACCAAAAATAATGAGCAGTTTCGCCACTGACAAGGCA
(SEQ ID NO: 2)

d3-169
Chr9: 37611591
AAGAGGATTTCTTTGGAGGAAGCAGCTGGTGTGCTAAGTGCCGCTCATGG
CCCCAGGGGATAAGGAAGGGGTGTGTGGGTGCCTATCTCACCTCACTTCA
GCAGGACCACTCAGAGCTTGAGCTGTGTCTCCTGCAGTTGGGGGCCCAGG
GGACTGGGTCTGACTCCCRCCCTGGAAATTTACAGGAAAAGAGCAGGGCT
GGCTAATGCTTTGGCTG
(SEQ ID NO: 3)

r3-116
Chr9: 37618560
CAGAGAAAAAGAAAGGAGGAGGAGGAGGAAAGAGAAGTCAAGTTTTAAAA
GCAAACAGAAATAATAGTTTTGATGGGATGGATTTGTTTTCTTAATAAGC
CTAATGATCCCAGGAKTCTCATTGGATTATTAGCAACTGTATTTAAAATT
TAAATCTAAAACAAGTTTTGTAGCTGCAAAGTGCTTATCAGAACCTAACC
ATGCCTCTCTGGCT
(SEQ ID NO: 4)

14-70
Chr9: 37634719
AGAGCTCAGTTTCCCAAATAAACCTGAATCTGAATCCCATTTACCAGCTC
TGTGACCTCATACCAGTCGYTTGAATTCTCTGAGCTTGCCTCAGTTTCAT
CTGTGAAGTGGGGATTGTCATGTGTGTCCTGCCTAACTCAAGCAGCTGTT
GAGAGAATAAGATGAGATGATTGCTCTGTTTGGTGTTTTACAAACTGAAA
(SEQ ID NO: 5)

m4-218
Chr9: 37635098
TAGTGCTAGAGAGGGTGGCATCTGCCCCCGGGGGCTGTGGGGAGCACGGT
GGGTAGTGGGGAGTTGCAGTCACCCAGCAGATGCAAAGCAGAATGAAGCCT
ATGGGAAGTGGCCAGATGTAGTTGTCAAGACCAGGGTAGGGCCACACTTG
ATGCTGGCCACAACCTCAAGACATGCCTTCTTCTGGGGAGCTGATCTCCC
AGGAGCTGAGCCAGCAGRAAAAAAAAAAAAAGAGAG
(SEQ ID NO: 6)

x4-77
Chr9: 37639129
AGGCTGACACTGACGCAGGTAGCTAGGAAATGGAGGGGACAGGGCAAAA
TTCCATGGGAACATTTGTACTCACCRGACAAGAGAATAGTTCTTATCTT
ACTTTCTGACAAGTGCTATGCTTTTTGGTGTTTAACTGCCTTGGAGAGAG
TAATTTGATGATTAATCTTTATCTACAAAATAATTTTTAAAATTAAACTT
TATTTTGAGAAAATTGTAGATTCA
(SEQ ID NO: 7)

z4-66
Chr9: 37639690
AAGTGCTGCTAGTCTTCCCCCACCGCCCTTGGATGAAGGATGCACTTGTT
AACATCTGCCTGTGCRCCATCCCCAGAATGATCTAACATCCCAGTCTGAT
GGTGCCTCAACCCTACTCAGAACTCCTCCCATGAACCTGCCAGTGCACTG
GGAACACGGTGCAAACTCCTTGACCAGGAATTGCCCCTGCTGACTCCCC
(SEQ ID NO: 8)

f5-152
Chr9: 37643111
AGGTGGTGAGGAATAGAAAGGCTATGTGTAGGTCAAGGAGCTGGTACGAG
CAAGGAACTGGTGAGAGCTGGGAGAGCATGAGACAGATGAGAGCAGTGAG
CCTGGTGGAAGCACAGAGAAGGCAGAGCACTTCAGAGACAGGGCAGCGGG
ARGAGGCTCTGGAGGCTCTGAACCTGGGCTGGAATCCTCGCTGGCTGTGG
(SEQ ID NO: 9)

y5-43
Chr9: 37650583
ATTTCTCTTAAAGAACAGTGATTTTAAAGTAGGTTTAAACAAYGGGTTTA

AAGAACAGTGATTTTCCATTTTGACAAGGCTTGTTTGGTATAGCCACTTC
AAAATATCCCCACATCAAAATATGATGCTTTATCTGGGATATCTTTTCCA
GACTTTGGGAGCCTTCCCTCCTGCACTTTCATTTCTGCAAGGCAATACTC
(SEQ ID NO: 10)

i6-31
Chr9: 37655211
CAACATATTTGTAATACAGACATCGAAAATAAACCAAATATCCAGCAATA
GGGACTTAGCTTTAAAAATGGCACTCTTATCTATAGCAAATAAACAATAA
TGTTGTAGAATAATAAAGACACAGGGAAATGTTTACAGTGTATATTTTC
AGTTTAGAAACCAGCATATATGGTAAGTTCCCAATTATGTTGAAAATGTG
TCTTTTCACACWAAAAGACTGGAAGAGTAATTAGCAACTTATAGCTTTTA
GTGGACAATTTTTATTATCTTCTCTCCAAAAAAGAAAACTTTCAAAATTT
TCTACCAGCCACATGTATTACTTTTATAAGAGGGAGGAAATAAGTGACAA
TTAAGAAAAAGAGATAAGCTTTTGGAGAGCGTTGTTTGAGCGTCACTAGG
(SEQ ID NO: 11)

i6-103
Chr9: 37655573
TGGAAAACTAATGAGCACATCATTTATCTTGCAAATTCCAGACAGGTGGT
GTTTTCAGAAGGAAGAGTGGTCTTAGGTCCATTTGTGTGAGTATATTTAT
AGAAGTGAAAGCTTTGGGGGAAGGAAATAGATTGATTTTTTCCCCTTGA
ACTTCTGAAATTATTTTTTCCRCTCCATTTGTAATTGAGCCCAGGGAGCT
ATTCTTATTTCTTCCTTTCTTGGGCACTGCGTTAGACCTAAAAATGTTAA
CTGGCTTAGGATGTGGGTTTTGCTAAAATGATTCCCCTTGAAGTCTTCAC
TGGGCTTTCTCATGCTTAAAAGTGGGGTCCCGCAGAAGATCACTTTCTAC
CTAATGCACTTTGCTCCTGAAGTCTTTGGCAACGTTGGGGTGGTCAGA
(SEQ ID NO: 12)

All chromosome positions are from the current NCBI build. These numbers will change with successive builds. However, the flanking sequence will allow others to identify these SNPs in the future.

B. Diagnostic Method

In one embodiment of the present invention, one would collect a DNA sample from a patient and genotype that DNA sample in order to estimate risk. For example, a patient's sample with at least one T allele of rs2182317 would indicate that the patient is at a lower risk for breast cancer than the general population.

We describe a preferable prophetic diagnostic method below. Of course, one of skill would be able to substitute similar method steps. The method is based on the same two SNPs, rs6476643 and rs2182317, that we used for our experiments described below.

Collect DNA from Individual:
Individual rubs cheeks against teeth with ~15 ml of SCOPE mouthwash in mouth for 30 seconds and rinses into 40 ml Nalgene container, repeat.

Extract DNA:
Collect mouthwash from individuals, transfer to a 50 ml Falcon centrifuge tube, and centrifuge in a JS-4.2 rotor at 3000 RPM (2000×g) at room temperature for 15 minutes. Pour off SCOPE and then extract DNA from pellet according to PUREGENE cell and tissue kit from GENTRA systems according to manufacturer's protocol. Sample should be stored at −20° C. after collection, cell lysis, or when sample is in isopropanol.

Genotypinq:
Use 5 ng of individual's genomic DNA in ABI SNP genotyping assay according to manufacturer's protocol. Plate must be read on ABI 7700 or 7900 instruments with SDS software. One of skill in the art would understand that there are numerous methods to characterize SNPs. Any accurate method of genotyping would be suitable for the present invention.

One would examine the DNA for the presence or absence of the minor alleles listed in Table 1 or minor alleles correlated with these alleles. The rs numbers listed in Table 1 and Table 2 and throughout the application are listed in a public database (NCBI, National Center for Biotechnology Information) and refer to a specific location in the genome where two different bases (A, T, C, or G) are found in a particular position in the human population. When looking at the sequences (as opposed to the rs numbers) we supply with Table 1, the IUPAC letters indicate a polymorphism, i.e. R=A or G, Y=C or T, M=C or A, K=T or G, W=T or A, S=G or C. ~99.9% of all bases are identical in all people. While any individual can have a mutation that is extremely rare (for example one person has the base change in millions of people) at any given position in the human genome, there are some specific sites that vary in many people. A base variation is considered a SNP if the rare base is found at a frequency of 1 in 100 chromosomes. The less common base variation is called the "minor allele."

The genotype of the sample determines the risk prediction. Women who are heterozygous (G/T) or homozygous (T/T) for the minor allele at SNP rs2182317 have a 14% reduction in risk. Women who are homozygous for the minor allele of rs6476643 (T/T) have a 19% increase in risk. The polymorphisms listed in Table 2 can also be used to predict risk. The alleles associated with risk are listed in the Table as well.

Risk Assessment:

Our data indicate that the minor allele of rs6476643 in the MCS5A1 region acts in a mostly recessive manner to increase risk by ~19% in ~6% of women. Within the MCS5A2 region the minor allele of rs2182317 acts in a dominant manner to decrease risk by 14% in ~24% of women.

Use of Other SNPs

We have characterized susceptible and resistant individuals using SNP rs2182317 to estimate resistance and rs6476643 to estimate susceptibility. However, one could genotype other SNPs which are correlated to either of these SNPs (most preferably $r^2>0.9$, preferably $r^2>0.7$) to characterize the experimental sample. In one method, one would sequence regions and discover previously unidentified polymorphisms and then genotype a set of people for these new polymorphisms including our two and then haplotype all individuals. Individuals can be haplotyped for all genotyped SNPs including rs2182317 and rs6476643 by use of a statistical program such as PHASE (Stephens, M., and Donnelly, P., *Am. J. Hum. Gene.* 73:1162-1169, 2003; Stephens, M., et al., *Am. J. Hum. Gene.* 68:978-989, 2001). Other polymorphisms can be tested for correlation with rs2182317 or rs6476643 with the $r^2$ statistic (Weir, B. S., 1996, *Genetic Data Analysis*, Sinaur).

Polymorphisms with a high correlation to our two SNPs ($r^2>0.7$) should replicate the same association pattern. Also, any polymorphisms on Chromosome 9 between the SNPs rs10973432 and rs12554736 with allele frequencies smaller than rs2182317 that are exclusively or mostly present in individuals who carry the minor allele of rs2182317 may replicate the pattern if they are in fact the causative polymorphism.

C. Therapeutic Target

The FBXO10 and FMRPD1 gene loci products (i.e. the entire genomic sequence including exons, introns, promoters, and 3'-end) would be useful as a target for chemoprevention or therapeutic drugs. Other FBXO10 and FMRPD1 gene loci instantiations may be non-coding RNAs (ncRNA), cis-regulatory elements, enhancers, silencers, splice modifiers, etc.

Another embodiment of the present invention is a therapeutic intervention mimicking the biological effect of FBXO10 and FMRPD1 gene loci alleles that decrease/increase susceptibility to breast cancer, preferably using small molecules. Experimental evidence suggests that these drugs would be efficacious for all members of the population since there is a dosage effect seen with the Mcs5a1 and Mcs5a2 resistance alleles in animal studies. Therefore, the drug target would be FBXO10 and FMRPD1 gene loci products and other biological molecules that work in the same mechanistic pathway.

In one embodiment, this method would comprise a method for assaying for modulators of the FBXO10 and FMRPD1 gene loci products, consisting of the steps of exposing the FBXO10 and FMRPD1 gene loci products to test compounds and determining whether the test compound mimics the biological effect of FBXO10 or FMRPD1 alleles that decrease susceptibility to breast cancer. In one embodiment, this would be done by determining gene loci that are differentially expressed between primary mammary cell cultures derived from WKy and WF parental strains using gene expression array analysis. A subset of differentially expressed gene loci would become indicators for drug screening assays. The promoters from the selected reporters would be placed in a reporter gene construct using standard molecular biology procedures and transfected into cultured mammary cells. The drug screening assays would involve exposing transfected mammary cells to a panel of small molecules and monitoring expression of the reporter gene contained within the construct. Those drugs that yield a similar pattern of reporter expression similar to the WKy strain would become lead candidates for further development and in vivo testing.

The following are proposed therapeutic targets:

Target 1—F-Box Motif of FBXO10: disrupt or enhance the FBXO10 interaction with the ubiquitin-conjugating enzyme. This could be done with small molecules to inhibit the protein-protein interaction between FBXO10 and the ubiquitin-conjugating enzyme. Antisense-RNA targeting FBXO10 and/or the conjugating enzyme could be used to disrupt the interaction.

Target 2—Target Specificity Domain of FBXO10 disrupt or enhance the FBXO10 interaction with its specific biological target(s). F-Box proteins have evolved to function as cell regulatory ligases. The regulatory function is achieved by having a target specificity domain in addition to the conserved F-Box. The target specificity domain serves as a binding domain for specific biological molecules that the F-box protein regulates. Therefore, the interaction between FBXO10 and the gene it regulates would be a target for drugs and antisense-RNA.

D. FBXO10 and FMRPD1 loci as a probe to find biological molecules acting in the same mechanistic pathway In another embodiment of present invention, one would use the FBXO10 and FMRPD1 gene loci as probes to identify other biologically important molecules. One would seek to identify molecules that interact with and act in the same biological pathway as the FBXO10 and FMRPD1 gene loci using the FBXO10 and FMRPD1 gene loci as probes. In one embodiment of the present invention, one would assay molecules for their ability to interact with the FBXO10 and FMRPD1 gene loci or the FBXO10 and FMRPD1 gene loci products.

FBXO10 is an F-Box protein, which indicates it functions biologically as a ligase to ubiquitinate, thus regulates specific targets within the cell. Therefore, there are at least two other gene products with which FBXO10 has direct interaction. The function of the F-Box motif is to provide a link between the ligase and the ubiquitin-conjugating enzyme. F-Box proteins have evolved to function as cell regulatory ligases. The regulatory function is achieved by having a target specificity domain in addition to the conserved F-Box. The target specificity domain serves as a binding domain for specific biological molecules that the F-box protein regulates. Based on this evidence and because of the specificity FBXO10 gene locus will provide, the locus is the best biochemical probe to identify the upstream and downstream interacting genes.

Proposed Methods

Yeast Two Hybrid Screen for Mcs5a interacting proteins—Yeast two hybrid screens in which different segments of the FBXO10 and FMRPD1 gene loci products are used as bait would be useful to screen for specific proteins that interact with various domains of FBXO10 and FMRPD1 loci products. For example, using the sequence that encodes the F-Box as bait would be expected to pull out the ubiquitin-conjugating enzyme. In a separate screen, the target specificity domain of FBXO10 used as bait would be expected to pull out the regulatory target of the FBXO10 locus.

Pull-Down Assays—In this assay the FBXO10 and FMRPD1 loci open reading frame sequence is placed in an expression vector that adds a detectable tag (i.e. GFP, FLAG, GST) forming a recombinant protein that can be captured on using an affinity ligand specific for the tag. This method allows the study of protein-protein interactions from their endogenous environment. It can be used to confirm interactions discovered in the yeast two hybrid screens and also as a discovery tool. As a discovery tool the pull-down assay can be useful to identify directly and indirectly interacting proteins because the entire protein complex may be co-purified. For verification the interacting protein can be tagged and immunoblotted with an antibody specific to the tag after coimmunoprecipitation of the protein complex. Or, if an antibody specific to the interacting protein is available, this can be used to confirm the presence of the interacting protein. For discovery, mass spectrometry could be employed to identify the proteins present in the complex.

Mammalian Two Hybrid Screen—This screen is similar to the yeast two hybrid system except that mammalian cells are used. The advantage is the false-positive rate is reduced.

Correlated Gene Expression—One method to find gene loci that act in the same molecular pathway would be to identify mRNAs that exhibit a positive or negative correlation with the expression patterns of the gene locus of interest. To do this, conditions that alter the mRNA levels of FBXO10 and FMRPD1 would be identified. Microarray analysis of gene expression would then be performed under the same condition to detect other gene loci that change in expression under the same condition. The gene loci that change in expression would then be considered as candidates acting in the same molecular pathway.

If the important genetic elements in the Mcs5a1 gene locus is an ncRNA, enhancer, splicing modifier, silencer, etc. then the approach would be to identify specific biological molecules being modulated by this element. This could be accomplished by comparing the gene expression profile between mammary glands of congenic rats with or without the modifier element.

EXAMPLES

Rat Mcs5a is a Compound QTL with Orthologous Human Loci that Associated with Breast Cancer Risk Abstract To identify human breast cancer risk genes, a rat mammary carcinogenesis model was used to positionally identify and characterize susceptibility loci. We identified a compound QTL, Mcs5a, which required a synthetic interaction of two elements, Mcs5a1 located within Fbox10, and Mcs5a2 within Frmpd1, to confer mammary cancer resistance. In two large case-control populations including ~12,000 women, the minor alleles of rs6476643 (SNP-A1) in MCS5A1 ($p=0.02$) and rs2182317 (SNP-3) in MCS5A2 ($p=0.0003$) associated with an altered risk of breast cancer. These results illustrate the complexity of breast cancer genetics while demonstrating the utility of rat models to identify unbiased candidates that associate with breast cancer risk.

Introduction

In order to further fine-map the Mcs5a locus, recombinant rat lines were collected and phenotyped for resistance to DMBA-induced carcinogenesis. Carcinoma development in DMBA-treated WKy-homozygous rats from congenic lines O, WW, and XX was reduced ~50% for each line (FIG. 1). The boundaries of the Mcs5a locus are given by the overlapping WKy sequences of congenic recombinant lines WW and XX, which define a genomic interval of ~116 Kb containing Mcs5a. Analysis of additional congenic recombinant lines within this interval demonstrated that at least two genetic elements exist within Mcs5a. They are defined by incorporating phenotype data from congenic lines LL and B3. These lines have a short interval of overlap (415 bp), and together cover the Mcs5a locus. Interestingly, WKy-homozygous rats from either line LL or B3 do not have a phenotype of resistance (FIG. 1). The simplest hypothesis to explain these data is that Mcs5a is a compound locus containing two genetic elements, Mcs5a1 and Mcs5a2, which interact synthetically to confer the Mcs5a mammary cancer resistance phenotype.

Mcs5a1 is defined by the overlapping genomic region of congenic lines WW and B3, which is ~32 Kb (~30 Kb in humans). Mcs5a1 contains mostly intronic sequence of the uncharacterized Fbxo10 gene, which contains an F-Box domain. F-box proteins are components of SCF complexes (ubiquitin ligases). The Mcs5a1 region contains a small section of intron 1, the small exon 2, and the majority of intron 2 of the Fbxo10 gene. Resequencing the WF and WKy alleles of Fbxo10 exon 2 revealed no nucleotide differences. However, resequencing of the entire Mcs5a1 region, using gDNA from WF and WKy rats, identified 90 SNPs and 28 indels within the Fbxo10 intronic sequence of the Mcs5a1 locus. This observation supports a search for potential Mcs5a1 candidates within the intronic sequence of the Fbxo10 gene. Several known mammary expressed transcripts map to the Mcs5a1 region within the Fbxo10 intronic sequence (FIG. 1).

When assayed by quantitative RT-PCR with two different Fbxo10 TaqMan™ probes, no significant differences in mRNA levels were found in mammary gland tissue from 12-week-old virgin rats homozygous for the Mcs5a WKy allele versus those homozygous for the Mcs5a WF allele. Similarly, no significant differences in Fbxo10 mRNA levels were found in mammary glands of DMBA-exposed rats.

Mcs5a2 is defined by the overlapping genomic regions of congenic lines LL and XX and covers ~84 Kb (~63 Kb in humans). This locus spans a region from within the first intron of Fbxo10, including its first exon and proximal promoter, to a location between the 5' UTR and the first coding exon of the uncharacterized gene, Frmpd1 (FERM and PDZ domain containing 1). No difference in the amino acid sequence encoded by the first exon of Fbxo10 was identified between WKy and WF rats. Analysis of Frmpd1 expression in mammary gland tissue identified no differences in mRNA levels in rats at 12 weeks or after DMBA exposure. In addition, the nucleotide sequence of the transcribed Frmpd1 5' UTR is identical between the WF and WKy rat strains.

We localized the human region that is orthologous to the rat Mcs5a locus (Mcs5a1 and 5a2) to ~93 Kb on human chromosome 9 and determined the human haplotype block structure of a 1 Mb region surrounding this area. Haplotypes from a single block in the MCS5A locus were tested for association with breast cancer risk in a Wisconsin case-control study (1,500 cases; 1,405 controls). Allele 4, a subregion of this block that spanned SNPs rs10758440, rs999988, rs2182317, rs2381718, was found to be marginally significant in the Wisconsin population. These four SNPs were then evaluated in the larger UK population (4,364 cases; 4,547 controls). Table 2 summarizes the results, which demonstrate a highly significant association of the minor allele of rs2182317 (SNP-3) with a reduction in risk of developing breast cancer. The Wisconsin and UK populations combined (N=11,779 women) yielded a heterozygous odds ratio of 0.86 (0.79-0.94), and a homozygous odds ratio of 0.77 (0.57-1.04). The uncorrected Chi-square trends test, stratified by study, yielded a P value of 0.0003 (Table 1), and when corrected for multiple comparisons using the conservative Bonferroni method the P value was 0.001.

Polymorphisms highly correlated to SNP-3 could include the causative polymorphism(s) for the association to breast cancer risk. To locate correlated polymorphisms, the human-rat conserved non-coding sequence (CNS) segments within MCS5A2 (~27 Kb total sequence, ~30% CNS) and the entire MCS5A1 region (~30 Kb) were resequenced in 24 women from the Wisconsin case-control population (12 cases; 12 controls). These samples were chosen to represent the haplotype allele frequencies observed in the population.

Figure 2:
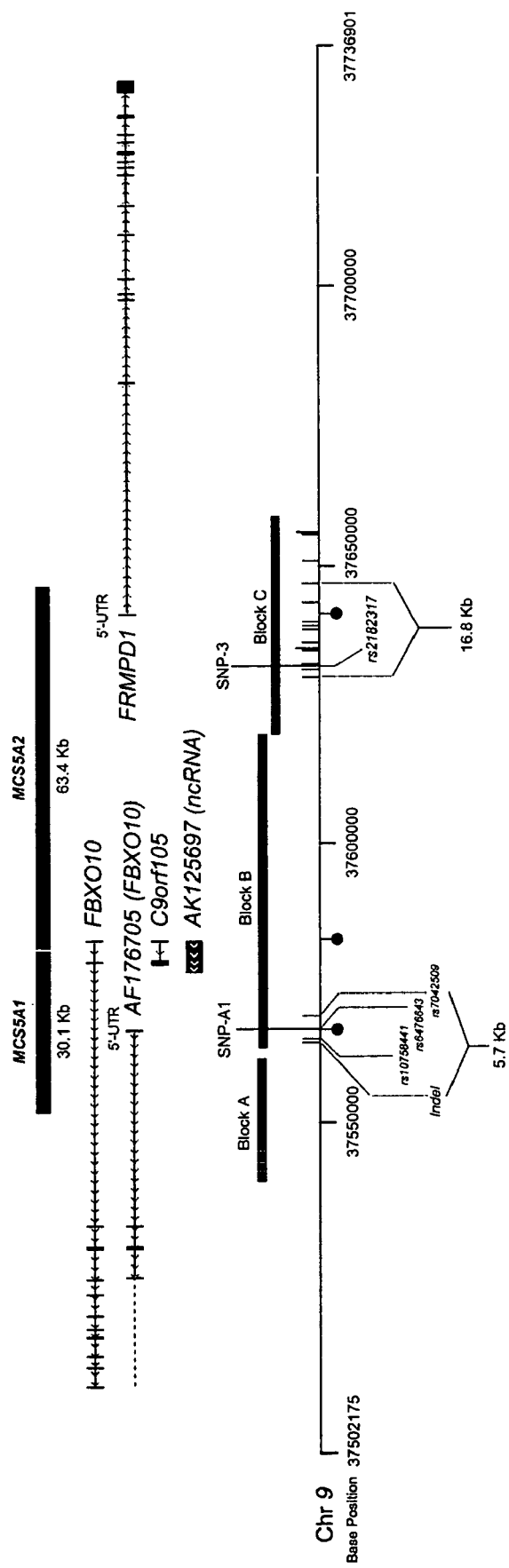
FIG. 2. The human MCS5A1 (30.1 Kb) and MCS5A2 (63.4 Kb) loci contain breast cancer-associated polymorphisms. The genomic regions shown on human chromosome 9 are orthologous to the rat Mcs5a1 and Mcs5a2 regions. MCS5A transcripts present in human tissue are mapped as exons connected by intronic sequence. Haplotype blocks that overlap MCS5A contain the breast cancer risk-associated polymorphisms, SNP-A1 (rs6476643) in MCS5A1 and SNP-3 (rs2182317) in MCS5A2. Association of these SNPs to breast cancer risk was determined using two population-based samplings that evaluated ~12,000 women. The minor allele frequency of SNP-A1 (MCS5A1) was 0.25. SNP-A1 was associated with an ~19% increased risk to breast cancer for women that are homozygous for the minor allele. The minor allele frequency of SNP-3 (MCS5A2) was 0.13. SNP-3 associated with an ~14% decreased risk to breast cancer for the 24% of women that carried at least one minor allele. The polymorphisms that correlated (high $r^2$) with SNP-A1 are in the 5.7 Kb region marked by brackets within the MCS5A1 region. The SNPs correlated (high $r^2$) with SNP-3 that lie within the human/rat MCS5A2 orthologous region are within a 16.8 Kb bracketed region. The x-axis is the human chromosome 9 base position based on the May 2004 UCSC human genome assembly. The x-axis marks designate SNPs, INDELs, CpG islands, and chromosome 9 base positions.

After resequencing, haplotype block 4 was separated into haplotype blocks A, B, and C (FIG. 2) based on $r^2$ estimates. We found no polymorphisms in the resequencing data of the MCS5A1 region that correlated to SNP-3. We did find 12 SNPs, highly correlated to SNP-3, in the MCS5A2 region that localized to a ~17 Kb interval, which is ~40 Kb distal to the MCS5A1/5A2 boundary (FIG. 2). This ~17 Kb sequence covers a region upstream of FRMPD1 to an interval that includes its 5' UTR exon (FIG. 2). It is likely that the MCS5A2 causative genetic alteration resides either within, or in close proximity to this reduced interval.

(SNP-3 (rs2182317) and other polymorphisms listed in the bin are candidates for the causative SNP(s) in MCS5A2. These candidates include many highly correlated SNPs that are heterozygous in all individuals carrying, exclusively, allele 4 of haplotype block 4.2. Any SNP-3 correlated SNP, or SNP combination, found in individuals carrying haplotype block 4.2 allele 4 could be the causative SNP. We hypothesize that the causative SNP is in or near a conserved region; thus, the genetic variation in our database may effectively narrow the region containing the causative SNP to chr9:37,610,247-37,655,573.

Considering all SNPs that are more rare or more common than SNP-3 and found in carriers of haplotype block 4.2 allele 4, the possible candidate SNPs include: 114-117 (MAF=~0.02-0.04), d3-169, rs12378421, r3-116, rs17505776, rs4878708, rs4878709, rs4878710, rs10973450, l4-70, m4-218, rs4490927, x4-77, z4-66, f5-152, rs4878713, y5-43, i6-31, and i6-103. Testing these SNP-3 correlated SNPs individually will not, by itself, distinguish one of these SNPs as the causative SNP in MCS5A2. This is because all but one of these SNPs, 114-117, has an identical or very similar minor allele frequency and distribution to rs2182317. There were only two SNPs, 128-249 and a correlated SNP 105-3, in MCS5A1 in which the minor alleles were found only in individuals with haplotype block 4.2 allele 4. The SNP 128-249 (MAF 2%) was not associated with a reduction of breast cancer risk; thus, the only causative SNP-3 correlated SNP candidates reside in MCS5A2.).

Like the rat model, no SNPs were identified within the FRMPD1 5' UTR in the human samples. Interestingly, resequencing of the distal ~36 Kb conserved regions of Mcs5a2 in the rat strains revealed that polymorphisms between the WKy and WF sequence occur only in the region orthologous to the SNP-3 correlated SNP region in the human (FIGS. 1 and 2).

We tested the additional genetic variation, revealed after resequencing the human regions, to determine if a polymorphism within MCS5A1 that was not correlated to SNP-3 in the MCS5A2 region associated independently with breast cancer risk in women. A total of 48 human chromosomes were resequenced at the MCS5A1 locus. Seventy-two (19 not listed in dbSNP) MCS5A1 SNPs with a minor allele observed in more than a single individual were documented. These SNPs were "binned" into groups of polymorphisms that were highly correlated to each other.

Bins were screened for an association with breast cancer risk in the Wisconsin case-control population. The results (Table 2) identified one bin (rs6476643, rs10758441, rs7042509, and an indel, 138-9899, on chr9:37563886-37563887) that qualified for further testing in the second population. One SNP from this bin (rs6476643, SNP-A1) was evaluated further in the UK breast cancer case-control population. The combined results for SNP-A1 yielded an odds ratio of 1.05 (0.97-1.13) for heterozygotes and 1.19 (1.03-1.38) for minor allele homozygotes (Table 2). A trends test, stratified by study, was significant for the minor allele (P=0.022). The polymorphisms in this bin are not highly correlated to any other variation; therefore, one of these polymorphisms is likely causative (The SNP bin that includes rs6476643 (SNP-A1) contains 4 polymorphisms with similar minor allele distributions but slightly different minor allele frequencies.

The minor allele of rs6476643 was found 84% of the time in women with haplotype block 4.2 allele 3, and 27% of the time in women with haplotype block 4.2 allele 1. The SNP bin including rs6476643 is close to an area of recombination and spans ~6 Kb. No SNPs correlated to this bin were found outside of this 6 Kb MCS5A1 region. This result is based on the distribution of the minor alleles found in the resequencing effort. Only one other SNP bin had minor alleles found mostly in haplotype block 4.2, allele 3. This SNP bin marked by SNP 24-131 has a minor allele frequency of 3%, and was found in 16% of women who have haplotype block 4.2, allele 3. However, this SNP did not show an association with breast cancer risk. The indel 138-9899 is correlated to rs6476643 ($r^2$=0.9). This correlation was not observed in the resequencing data because heterozygous and homozygous individuals for the deletion could not be distinguished (i.e., both appear as homozygous for the deletion). When tested using allelic discrimination, this polymorphism showed a trend towards resistance in the Wisconsin population with a P-value of 0.22).

The human sequence variation correlated to SNP-A1 (rs6476643) in MCS5A1 is located at the beginning of haplotype Block B, and the variation correlated to SNP-3

(rs2182317) in MCS5A2 is located in haplotype Block C (FIG. 2). The SNP-A1 cluster spans ~6 Kb of human chromosome 9 and contains a CpG island located at a transcriptional start for a potential candidate gene identified in the rat and human (AF176705) (FIGS. 1 and 2). AF176705 encodes two breast cancer modifier alleles by taking advantage of natural genetic variation in model organisms, reinforces the possibility that a sufficient number of modifier alleles can be identified using similar methods to impact breast cancer risk estimation in women.

TABLE 2

Breast Cancer Risk Associated SNPs in MSC5A1 and MCS5A2
Genotype frequencies and genotype-specific risks in 5848 women with breast cancer and 5931 controls from Wisconsin and the UK.

|  | P-values Trend (1df) Heterogeneity (2df) | Series | Major allele frequency | Minor allele frequency | Major Allele homozygote No. (%) | Heterozygote No. (%) | Minor Allele homozygote No. (%) | Number genotyped |
|---|---|---|---|---|---|---|---|---|
| MCS5A1 SNP-A1 rs6476643 |  |  |  |  |  |  |  |  |
| WISC | 0.058 | Cases | 0.72 | 0.28 | 778 (53) | 590 (40) | 113 (8) | 1481 |
|  | 0.143 | Controls | 0.75 | 0.25 | 765 (55) | 532 (39) | 84 (6) | 1381 |
|  |  | OR (95% CI) | 1 (ref) | 1.12 (1.03-1.22) | 1 (ref) | 1.09 (0.93-1.27) | 1.32 (0.98-1.78) |  |
| UK | 0.123 | Cases | 0.74 | 0.26 | 2373 (55) | 1657 (38) | 316 (7) | 4346 |
|  | 0.230 | Controls | 0.75 | 0.25 | 2517 (56) | 1704 (38) | 290 (6) | 4511 |
|  |  | OR (95% CI) | 1 (ref) | 1.05 (1.01-1.11) | 1 (ref) | 1.03 (0.94-1.13) | 1.16 (0.98-1.37) |  |
| Combined | 0.022 | Cases | 0.73 | 0.27 | 3151 (54) | 2247 (39) | 429 (7) | 5827 |
|  | 0.049 | Controls | 0.75 | 0.25 | 3282 (56) | 2236 (38) | 374 (6) | 5892 |
|  |  | OR (95% CI) | 1 (ref) | 1.07 (1.01-1.13) | 1 (ref) | 1.05 (0.97-1.13) | 1.19 (1.03-1.38) |  |
| MCS5A2 SNP-3 rs2182317 |  |  |  |  |  |  |  |  |
| WISC | 0.140 | Cases | 0.89 | 0.11 | 1166 (79) | 291 (20) | 15 (1) | 1472 |
|  | 0.126 | Controls | 0.88 | 0.12 | 1074 (78) | 284 (21) | 26 (2) | 1384 |
|  |  | OR (95% CI) | 1 (ref) | 0.89 (0.75-1.04) | 1 (ref) | 0.94 (0.78-1.13) | 0.53 (0.28-1.01) |  |
| UK | 0.001 | Cases | 0.89 | 0.11 | 3436 (79) | 878 (20) | 62 (1) | 4376 |
|  | 0.003 | Controls | 0.87 | 0.13 | 3430 (75) | 1045 (23) | 72 (2) | 4547 |
|  |  | OR (95% CI) | 1 (ref) | 0.86 (0.81-0.92) | 1 (ref) | 0.84 (0.76-0.93) | 0.86 (0.61-1.21) |  |
| Combined | 0.0003 | Cases | 0.89 | 0.11 | 4602 (79) | 1169 (20) | 77 (1) | 5848 |
|  | 0.0016 | Controls | 0.87 | 0.13 | 4504 (76) | 1329 (22) | 98 (2) | 5931 |
|  |  | OR (95% CI) | 1 (ref) | 0.86 (0.80-0.94) | 1 (ref) | 0.86 (0.79-0.94) | 0.77 (0.57-1.04) |  |

FBXO10, and two splice variants originate from the homologous CpG island in the rat. The SNP-3 cluster in MCS5A2 contains the putative regulatory region of FRMPD1, which is expressed in both rats and humans.

This study demonstrates the utility of a comparative genomics approach to identify DNA polymorphisms that can serve as risk markers of multigenic disease and to reveal the genetic complexity underlying common diseases. Complexity is illustrated in the rat compound Mcs5a locus that consists of at least two interacting elements Mcs5a1 and Mcs5a2. An analysis of the human homologous regions identified alleles from both MCS5A1 and MCS5A2 that associated with breast cancer risk. The minor allele of SNP-A1 in the MCS5A1 region acts in a mostly recessive manner, similar to the rat WF allele, to increase risk by ~19% in ~6% of women. Within the MCS5A2 region the minor allele of SNP-3 acts in a dominant manner, similar to the rat WKy allele, to decrease risk by ~14% in ~24% of women.

The Mcs5a elements responsible for altering cancer risk may not reside in protein coding sequence in either the rat or human. While the percentage of non-protein coding elements contributing to the risk of complex diseases is unknown, other such elements have been associated with disease risk (E. S. Emison et al., Nature 434, 857 (2005), G. G. Loots et al., Genome Res. 15, 928 (2005). Thus, the identification of these Materials and Methods Animal Experiments Inbred WF and WKy rats were obtained from Harlan Sprague-Dawley Inc. (Indianapolis, Ind.) and fed Teklad lab blox chow and acidified water ad libitum. Rats were maintained in a 12-hour light/dark cycle in an AALACC-approved facility and all protocols were approved through the University of Wisconsin Medical School Animal Care and Use Committee. Congenic lines were established and maintained as previously published (D. J. Samuelson et al., Carcinogenesis 24, 1455 (2003)). Congenics are defined as genetic lines developed on a WF genome and carrying the selected WKy alleles shown in FIG. 1. The congenic generations (number of backcrosses) used to determine the mammary carcinoma multiplicity phenotypes of lines O, LL, WW, XX, and B3 were N12, N14, N14, N15, and N15, respectively.

Primer information of the genetic markers and the SNP bp (rat genome June 2003 assembly available at the UCSC Genome Browser, www.genome.ucsc.edu) defining the ends of the WKy allele carried by each line are: lines 0, XX, and B3 proximal microsatellite marker gUwm40-18 FWP: 5'-GACT-TAATGTGGGGAGTGAA (SEQ ID NO:13), RVP: 5'-AG-CACATATGGAGGTTTGAC (SEQ ID NO:14); lines O, LL, and WW distal microsatellite marker gUwm45-5 FWP: 5'-CTAGAAAGGTGCTTTGGTTG (SEQ ID NO:15), RVP: 5'-TCAGCTTCTCCTCCTTCC (SEQ ID NO:16); line WW proximal SNP-A at chr5:61634906$^{C>T}$; line LL proximal SNP-B at chr5:61667232$^{A>G}$; line XX distal microsatellite marker gUwm23-29 FWP: 5'-CCAGTCTGATGACCT-GAGTT (SEQ ID NO:17), RVP: 5'-CTTGCATGTGTG-TAAGTGCT (SEQ ID NO:18); and line B3 distal SNP-C at chr5:61667646$^{G>A}$.

To determine mammary carcinoma susceptibility phenotypes, WF.WKy female rats aged 50-55 days that were WKy-homozygous or WF-homozygous for the selected congenic intervals were administered a single dose of 7,12-dimethyl-benz[a]anthracene (DMBA, 65 mg/kg body weight) (ACROS Organics; Fisher Scientific, Pittsburgh, Pa.) in sesame oil by gastric intubation, or were injected IP with N-nitroso-N-methylurea (NMU, 50 mg/kg body weight) (Ash Stevens, Detroit, Mich.). For Her2/neu experiments, female rats were infused with replication defective retrovirus containing the activated neu oncogene (pJRneu). The retrovirus was titered in vitro as previously described and $2.0 \times 10^5$ CFU/ml were injected into the central duct of each mammary gland. For detailed information on the pJRneu vector see (B. Wang, W. S. Kennan, M. N. Gould, *Cancer Res.* 51, 5649 (1991)). Mammary carcinomas≧3×3 mm were counted at 15, 17, and 8 wks post-induction for DMBA, NMU, and Her2/neu experiments, respectively. Mammary carcinoma multiplicity data were analyzed using the Mann-Whitney nonparametric test of StatView (SAS Institute Inc., Cary, N.C.).

Comparative Genomics

The Mcs5a rat chromosome 5 genomic region is based on the bp in the rat June 2003 genome assembly (UCSC Genome Browser) for the SNP at chr5:61634886$^{C>T}$ and the microsatellite marker (gUwm23-29) that mark the respective ends of the WKy Mcs5a allele delimited by the congenics. The Mcs5a proximal and distal rat chromosome 5 bp (chr5:61634886-61751793) and the VISTA browser (//pipeline.lbl.gov/) were used to find the human Mcs5a orthologous region on human chromosome 9 (chr9:37550841-37644624). Genes/genetic elements mapping to the region were found using the UCSC and VISTA Rat and Human Genome browsers.

Transcribed elements were verified using RT-PCR of total RNA from WF and WKy mammary gland and brain tissues. cDNA was synthesized from 2 µg total RNA for 2 hours at 42° C. in a 20 µl final reaction volume consisting of 0.5×RNA Secure (Ambion, Austin, Tex.), 0.05 µg/µl oligo(dT)$^{18}$, 125 µm dNTP mix, 1× first strand buffer (Invitrogen, Carlsbad, Calif.), 10 mM DTT, and 200 U Superscript II reverse transcriptase (RT) (Invitrogen). For PCR reactions, RT reactions were diluted 1:2 or 1:4 and a microliter of this dilution (~25-50 ng RNA equivalent cDNA) was used in a 20 µl PCR reaction. The reaction components were 1× Herculase Buffer (Stratagene, LaJolla, Calif.), 200 µM each dNTP mix, 500 nM each primer, and 1 U Herculase DNA Pol (Stratagene). PCR cycling conditions in a Biometra T3 thermocycler were 95° C. for 2 min, followed by 35 cycles of 92° C. for 1 min, 59° C. for 45 sec, and 72° C. for 2 min. A 5 min extension at 72° C. was added at the end. Human/Rat conserved non-coding sequences (CNS) in the Mcs5a2 region were identified using the VISTA browser with settings of 90 bp and 60% identity.

TaqMan Quantitative RT-PCR

TaqMan Quantitative PCR (QPCR) primers and probes (ABI, Foster City, Calif.) were designed using Primer Express v2.0 (ABI) according to manufacturer's specifications. Primer and probe sequences, respectively, were: Fbxo10 probe1: 5'-FAM-AGGCCTCATCACA-GAAAACGTCATCCG-TAMARA (SEQ ID NO:19), FWP: 5'-GCTGGCATAGCAGTGAACGA (SEQ ID NO:20), RVP: 5'-CTACACCTCCCCACTGGTTCTC (SEQ ID NO:21); probe 2: 5'-FAM-CTTTTCCCAGACCACATC-MGB (SEQ ID NO:22), FWP: 5'-CCAGCCTCTATGATCGAATCG (SEQ ID NO:23), RVP: 5'-CATTCTCAAAGTTGCAGT-TGTCAA (SEQ ID NO:24); and Frmpd1 probe: 5'-FAM-CCTTTCCACCACCTGCTG-MGB (SEQ ID NO:25), FWP: 5'-CGCCTACACCTMGCATGAG (SEQ ID NO:26), RVP: 5'-GCGGGAGTCCTGTGATTCTTC (SEQ ID NO:27). GAPDH probes from ABI were used as an internal control standard. Two-step TaqMan RT-QPCR was performed using mammary gland total RNA collected from virgin female WF and line O rats aged 12 wks. cDNA was synthesized as described above from 2 µg total RNA. For PCR reactions, RT reactions were diluted 1:8 and a microliter of this dilution (~12.5 ng RNA equivalent cDNA) was used in a 16 µl PCR reaction with ABI 7900 default cycling conditions. The reaction components were 1× TaqMan Buffer A (ABI), 3.5 mM $MgCl_2$, 200 µM each dATP, dCTP, dGTP, dTTP, 300 nM each primer, 200 nM TaqMan probe (ABI), and 0.4 U Taq Gold DNA Pol (ABI). PCR cycling conditions in the ABI 7900 were 50° C. for 2 min, 95° C. for 10 min, followed by 40 cycles of 95° C. for 15 sec and 60° C. for 1 min. FAM (Mcs5a region gene locus probe) and VIC (GAPDH probe) fluorescence values were measured using ABI SDS v 2.2 software when amplification reactions were in the linear phase; quantities of transcript were measured by comparison of $C_t$ values with those of serial dilutions used to calculate a standard curve. Measurements for each rat were an average of two replicates. Each quantity was standardized by dividing by the quantity of rodent GAPDH (ABI). Data were analyzed using the Mann-Whitney test of StatView (SAS Institute Inc., Cary, N.C.).

Rat Mcs5a Resequencing

To resequence gDNA regions, exons, 5'-UTR, and ORFs, primers spanning these elements were designed using Primer 3 (S. Rozen, H. J. Skaletsky, *Methods Mol. Biol.* 132, 365 (2000)). Spleen gDNA (~50 ng) or mammary gland cDNA (~25-50 ng) samples from WF and WKy rats were used as PCR templates. Spleen gDNA was extracted using previously published conditions. cDNA was synthesized as described above. The target gDNA or cDNA was amplified by the PCR conditions used for the verification of transcripts described above and gel-purified using Qiagen's (Valencia, Calif.) gel purification kit according to the manufacturer's protocol. One microliter of the gel purified suspension was used in each forward and reverse sequencing reaction (15 µl) that included 0.5 µl BigDye v3.1 (ABI), 1× reaction buffer (ABI), 0.67 µM primer. Conditions of the sequencing reaction were 95° C. for 3 min followed by 32 cycles of 95° C. for 30 sec and 58° C. for 2.5 min. A 72° C., 7 min extension was added at the end. The sequence reactions were processed using CleanSEQ magnetic beads (Agencourt, Beverly, Mass.) according to the manufacturer's directions. The final volume after cleaning was 50 µl. The sequence was determined by the University of Wisconsin Biotechnology Center (Madison, Wis.) sequencing facility from a 1:1 dilution of the sequencing reaction. Sequence data were analyzed using Sequencher v 4.2 software (Gene Codes, Ann Arbor, Mich.).

Wisconsin Human DNA Collection and Extraction

As part of an on-going epidemiologic study, we recruited population-based cases of incident invasive breast cancer and community controls from Wisconsin according to a protocol approved by the University of Wisconsin Health Sciences Institutional Review Board. Cases aged 20-69 years were identified though the Wisconsin statewide tumor registry. Controls were randomly sampled from driver's license files (ages 20-64 years) and Medicare beneficiary lists (ages 65-69 years). The controls were frequency-matched in five-year intervals to have a similar age distribution as the cases. All participants were required to have an available telephone number and no previous diagnosis of breast cancer. Prior to April 2003, when changes in federal law affected the willingness of physicians to acknowledge their care of our eligible participants, physicians (identified on the tumor registry reports) were contacted prior to case enrollment to obtain information that might contraindicate study participation, such as senility.

All participants were contacted by mail prior to receiving an interviewer's call. At the conclusion of the telephone interview, individuals were asked to provide a mouthwash rinse. Those agreeing were mailed a kit and instructed to rub cheeks against teeth and swish with ~15 ml of Scope (Procter and Gamble, Cincinnati, Ohio) mouthwash for 30 seconds and rinse into a 40-ml Nalgene container. They were instructed to repeat this 1×. For reasons of confidentiality, participants returned consent forms in separate envelopes directly to staff at the University of Wisconsin. For the Wisconsin sample population, 1,737 case and 1,790 control samples were collected. When samples yielded less than 5 µg of DNA, participants were asked to submit another sample.

Mouthwash from individuals was transferred to a 50-ml centrifuge tube and spun in a Beckman JS4.2 rotor @ 3000 RPM (2000×g) at room temperature for 15 minutes. Scope was poured off and DNA was extracted from the pellet using the PUREGENE cell and tissue kit from Gentra Systems (Minneapolis, Minn.) according to the manufacturer's protocol. DNA was hydrated in ddH$_2$O. The PicoGreen dsDNA Assay (Invitrogen) was used to determine DNA concentrations. Samples contained an average yield of 29.3 µg of DNA. UK samples are described (Anglian Breast Cancer Study Group, *Br. J. Cancer* 83, 1301 (2000)).

Construction of Haplotype Block Map for MCS5A

When data from congenic rat phenotyping first narrowed the Mcs5a region to 1 Mb, a haplotype block map of the human region was constructed. Ninety-one SNPs that spanned a 1 Mb region on chromosome 9 orthologous to the rat Mcs5a region were used to make a haplotype block map. The following SNP genotyping assays were available from ABI: rs6476611, rs1999142, rs7034763, rs2279556, rs7039784, rs1492713, rs10973239, rs13290794, rs2029646, rs12000309, rs2790063, rs3780334, rs186299, rs2087358, rs11793053, rs2235096, C__2013184_10, rs309444, rs1571234, rs1887455, rs3739576, rs2296775, rs10758435, rs17413120, rs7044153, rs4878697, rs13285217, rs10758440, rs2381718, rs1886909, rs12554736, rs13298495, rs7025444, rs10814604, rs2296553, rs1952125, rs10124071, rs2296552, rs12551499, rs7873508, rs1409145, rs1059059, rs7158, rs10973556, rs2005084, rs2025440, rs776018, rs1976936, rs12553058, rs1105773, rs943940, rs10973637, rs2183130, rs2890783, rs11790106, rs1928246, rs1928249, rs731841, rs2585668, rs1867178, rs645259, rs716933, rs3043, rs4878806, rs11361, rs2038589, and rs3849928. Twenty-four additional SNPs were chosen from the NCBI SNP database to narrow the distance between the SNPs from ABI. Twenty-one of these had minor alleles represented in the Wisconsin population and primer sequences are as follows:

rs3747539
forward primer-AGAACACTCTTCTTCCTTTTAGGTAAATGG
(SEQ ID NO: 28),
reverse primer-TGTGCTTTCCGTGTCTGGAATAAA
(SEQ ID NO: 29),
VIC-AAGAGCTGGAGACCAG(SEQ ID NO: 30),
FAM-AGAGCTGGAGCCCAG(SEQ ID NO: 31);

rs495304
forward primer-ACAGGATGACATAGTGAAGCTCTTATTAAAAAT
(SEQ ID NO:32),
reverse primer-ACACAATTTAAAATAACUGAGGCAGCAAG
(SEQ ID NO: 33),
VIC-CTCTAGATTTCCATTAGTAC(SEQ ID NO: 34),
FAM-CTCTAGATTTCCAATAGTAC(SEQ ID NO: 35);

rs3789019
forward primer-TTCAGGAGCTTGCAGTCTAGTTG
(SEQ ID NO: 36),
reverse primer-TTTCATCCTGCCTTGGACAATCA
(SEQ ID NO: 37),
VIC-ACGTCCACCGTCCCT(SEQ ID NO: 38),
FAM-ACGTCCACCCTCCCT(SEQ ID NO: 39);

rs2013458
forward primer-TCTGCAACAGCTATCAAAGTTTCTGT
(SEQ ID NO: 40),
reverse primer-ATGCATTTTGGAACAGTGCTTTCAT
(SEQ ID NO: 41),
VIC-AAAGCCAGGTGTATCTA(SEQ ID NO: 42),
FAM-AAAGCCAGGTATATCTA(SEQ ID NO: 43);

rs999988
forward primer-CCCCTCTGAACAGAGCCATTTTATA
(SEQ ID NO: 44),
reverse primer-CCACCTCTGTTTCCGCTAGAA
(SEQ ID NO: 45),
VIC-CATTAATGTTCAATTGAATTT(SEQ ID NO: 46),
FAM-ATTAATGTTCAATCGAATTT(SEQ ID NO: 47);

rs308492
forward primer-CGTTTGAAATGTGAATGCAGTCTGA
(SEQ ID NO: 48),
reverse primer-GTGCTTTCCAACATAGGGCAAAA
(SEQ ID NO: 49),
VIC-TCTCCAACAAAATAC(SEQ ID NO: 50),
FAM-CATCTCCAATAAAATAC(SEQ ID NO: 51);

rs1325916
forward primer-GGAGTATTGCCTTGCAGAAATGAAA
(SEQ ID NO: 52),
reverse primer-CCCCACATCAAAATATGATGCTTTATCTG
(SEQ ID NO: 53),
VIC-CCAGACTTTGGGAGCC(SEQ ID NO: 54),
FAM-CAGACTTCGGGAGCC(SEQ ID NO: 55);

rs3780335
forward primer-CCTTGTATGGGTTTAGGATGCAGAT
(SEQ ID NO: 56),
reverse primer-CCCACAGAGAGTCTTTAGCTTCAC
(SEQ ID NO: 57),
VIC-AGTTGGTGCTTTGACCTA(SEQ ID NO: 58),
FAM-TTGGTGCCTTGACCTA(SEQ ID NO: 59);

rs2182317 (SNP-3)
forward primer-TCCTACTAAACAGAAGCCCCTTGTA
(SEQ ID NO: 60),
reverse primer-CCAACATCCCCCAGTTACTTTCATT
(SEQ ID NO: 61),
VIC-ATTTACTCTGCTTATTCCTGT(SEQ ID NO: 62),
FAM-ATTTACTCTGCTTATGCCTGT(SEQ ID NO: 63);

rs309458
forward primer-CATTCGGTGTCCAGAGATTTCTGTA
(SEQ ID NO: 64),
reverse primer-CCTGTGGAAATCAAGGCTTCACTTA
(SEQ ID NO: 65),
VIC-CCTGGAATTCTGCTGCT(SEQ ID NO: 66),
FAM-CTGGAATTCCGCTGCT(SEQ ID NO: 67);

rs1033790
forward primer-CAGCCATGTAGAGAGACCAGATT
(SEQ ID NO: 68),
reverse primer-GGTTTTTCCCTCCCATTGTGTAGAC
(SEQ ID NO: 69),
VIC-ACTGAGCTTCAGTTCC(SEQ ID NO: 70),

```
-continued
FAM-CTGAGCTTCGGTTCC(SEQ ID NO: 71);

rs763936
forward primer-GGAGAAGCCATACTGAAGTGCAT
(SEQ ID NO: 72),
reverse primer-CCTTATTGCCCTAATGTTTTACTACAAATGC
(SEQ ID NO: 73),
VIC-CCTTGACATCTCCTTAAA(SEQ ID NO: 74),
FAM-CTTGACATCTGCTTAAA(SEQ ID NO: 75);

rs10511947
forward primer-GCATGGCAAGTGTCCAAGGA
(SEQ ID NO: 76),
reverse primer-TGTCCAAATCCCACCCAATCTTT
(SEQ ID NO: 77),
VIC-CAGAGTCATAAAGCC(SEQ ID NO: 78),
FAM-AGAGTCGTAAAGCC(SEQ ID NO: 79);

rs10511954
forward primer-CGGTTATCTCATGTCCAAAGCTCAT
(SEQ ID NO: 80),
reverse primer-CCACACTATCAATATGCCTGCTTCT
(SEQ ID NO: 81),
VIC-CAGCACATTAAAAGAA(SEQ ID NO: 82),
FAM-CAGCACATTAGAAGAA(SEQ ID NO: 83);

rs1885491
forward primer-TCGAACATCCCATAAAGCTCATTTCTT
(SEQ ID NO: 84),
reverse primer-TGGAAAGCCCAGCGGAATT
(SEQ ID NO: 85),
VIC-CCACTTTGAAGTGTTCTGT(SEQ ID NO: 86),
FAM-CACTTGAAGTATTCTGT(SEQ ID NO: 87);

rs1138374
forward primer-CTTACGAACCTGAAGGCCAAAG
(SEQ ID NO: 88),
reverse primer-GGGCCTGTCGTCATCCT
(SEQ ID NO: 89),
VIC-TGTTGACTCAGACTCGGA(SEQ ID NO: 90),
FAM-TTGACTCGGACTCGGA(SEQ ID NO: 91);

rs1928233
forward primer-CGCAGTCAAACCAGACATCATC
(SEQ ID NO: 92),
reverse primer-CAAGATACTGCCCTTTGTGGGATAT
(SEQ ID NO: 93),
VIC-TGTAGAACCCTGACAATG(SEQ ID NO: 94),
FAM-TAGAACCCCGACAATG(SEQ ID NO: 95);

rs920707
forward primer-GCAATGTCTTACCCCAAAGCAAGAT
(SEQ ID NO: 96),
reverse primer-TGAGGGTCCTGGAGGTATTCG
(SEQ ID NO: 97),
VIC-CCCCATCATCTCATC(SEQ ID NO: 98),
FAM-CCCCATCGTCTCATC(SEQ ID NO: 99);

rs1004604
forward primer-AGACTCAGTACATTATTAGAAATGCCTTTCAC
(SEQ ID NO: 100),
reverse primer-ATGGAAATGTCAACTTCATTGTCCCTAT
(SEQ ID NO: 101),
VIC-AACTGTTTTATTTGTTAAATGTTA
(SEQ ID NO: 102),
FAM-CTGTTTTATTTGTTAGATGTTA
(SEQ ID NO: 103);
rs885431
forward primer-CACAGCACAGGTGTGACTTG
(SEQ ID NO: 104),
reverse primer-CCTGCATCTTTTATGTGTCCTGGAA
(SEQ ID NO: 105),
VIC-CATGCCTTCCTTGGAGTA(SEQ ID NO: 106),
FAM-ATGCCTTCCTTGAAGTA(SEQ ID NO: 107);

rs2073478
forward primer-ATGGCGCCGGATGGAT
(SEQ ID NO: 108),
reverse primer-CTCGATCCCGCTCCACTAG
(SEQ ID NO: 109), -continued
VIC-CCAGGCGGTTCAG(SEQ ID NO: 110),
FAM-CCAGGAGGTTCAG(SEQ ID NO: 111).

Three SNPs from the NCBI database had no variation
in our population and are as follows:
rs2296556
forward primer-CAGGGATGAGGGTCTGAGTTG
(SEQ ID NO: 112),
reverse primer-CTCTTCCAGGGCTAAAGTTGCT
(SEQ ID NO: 113),
VIC-CTGATGGGCCCGCCAG(SEQ ID NO: 114),
FAM-CTGATGGGCCCACCAG(SEQ ID NO: 115);

rs717739
forward primer-CCACTTAAAAAACAAAGGGCCAAGTA
(SEQ ID NO: 116),
reverse primer-AGTTGTCTAGAGACTTGGGTTTCAGA
(SEQ ID NO: 117),
VIC-CCTAGAGCAACTTC(SEQ ID NO: 118),
FAM-ACCTATAGCAACTTC(SEQ ID NO: 119);

rs913282
forward primer-CCACAGGCAAGAATTCCAAATGAC
(SEQ ID NO: 120),
reverse primer-GCTGCCTGACCATCAACACT
(SEQ ID NO: 121),
VIC-TTCTATCCATGGAAGCAA(SEQ ID NO: 122),
FAM-ATCCGTGGAAGCAA(SEQ ID NO: 123).
```

To determine the linkage in the region, 39 CEPH (Centre d' etudes du Polymorphisme Humain) family grandparents (unrelated individuals with DNA available from the Coriell Institute and a selection of 100 case-control high-DNA-yield samples from the Wisconsin population were used to estimate the haplotype phase of 88 SNPs. Ten CEPH families (each including four grandparents along with two parents and two children) were genotyped and then haplotyped by inference from pedigree information. CEPH grandparents and 100 case-control samples were assigned haplotypes using the PHASE software package (M. Stephens, N.J. Smith, P. Donnelly, *Am. J. Hum. Genet.* 68, 978 (2001). PHASE, version 2.0). A comparison of the results of the PHASE software program and inferred pedigree information of all the CEPH family members was made to determine the accuracy of the haplotype estimates. Of the 79 CEPH family members, only 6 had haplotypes with discrepancies between haplotypes inferred from pedigrees and the PHASE output with the highest posterior probability. Out of 11 total discrepancies, 10 were "switch errors" in areas of low linkage disequilibrium and one "switch error" occurred in an area of high linkage disequilibrium.

Block boundaries were defined by areas of low linkage between adjacent SNPs. Linkage disequilibrium between each pair of SNPs was tested by calculating the Lewtonin D' statistic in the CEPH grandparents and Wisconsin case-control samples. Adjacent pairs of SNPs with a D' of $\geq 0.89$ were considered to be in the same block, while those with a D'<0.89 were not included in the same haplotype block.

Analysis of Polymorphisms in Haplotype Block 4

The initial 1 Mb interval containing MCS5A was subsequently narrowed, using additional phenotyping data from congenic rats, to an orthologous human region of ~94 Kb that was completely contained in block 4. Tag SNPs listed below in haplotype block 4 were genotyped in our Wisconsin case-control population (~1,500 cases and ~1400 controls). Twelve common haplotype alleles were observed in block 4. In order to reduce the number of haplotypes for testing, block 4 was divided into part 4.1, which had 4 major variants, and part 4.2, which had 7 major variants. The division between the second and third SNPs of block 4 resulted in the fewest haplotype variants.

Genotyping Human DNA Samples

Samples from the Wisconsin and UK populations were genotyped in 5 µl reactions using 5 ng of genomic DNA from the Wisconsin samples and 10 ng of primer extension preamplification (PEP) DNA from the UK samples using ABI SNP-genotyping assays according to the manufacturer's protocol. The following Tag SNPs were used for this analysis: rs4878697 and rs13285217 (tested in only the Wisconsin samples), and rs10758440, rs999988, rs2381718, and rs2182317 (tested in both the Wisconsin and UK case-control populations). Fluorescence levels were determined using an ABI 7900 instrument. Samples were amplified on MJ Research/Bio-Rad Laboratories (Hercules, Calif.) thermocyclers with conditions recommended by ABI. Genotyping results are in Table 2.

Statistical Analysis of Block 4 Haplotypes:

All common haplotypes in block 4 (four in 4.1, seven in 4.2) were screened using COCAPHASE v2.403 (F. Dudbridge, *Genet. Epidemiol.* 25,115 (2003). COCAPHASE v2.403), which calculates odds ratios and an overall p-value based on a likelihood ratio test. The haplotype block labeled 4.2 merited further investigation as a likely candidate, based on the odds ratio and 95% confidence interval. It is important to note that the minor allele of rs2182317 (risk reduction-associated allele SNP-3 in MCS5A2) was found only in allele 4 in block 4.2.

Statistical Analysis of Individual SNPs

The four tag SNPs that characterize the common haplotypes in block 4.2 (rs2381718, rs10758440, rs999988, rs2182317) were subjected to a battery of tests (i.e., Cochran Armitage test for trend and normal approximation of log odds ratios for heterozygotes and minor allele homozygotes) using a population of 4,376 breast cancer cases and 4,547 controls from the UK samples. The same tests were applied retroactively to the Wisconsin population, as well as the combined stratified sample.

Resequencing of MCS5A

The human gDNA region spanning MCS5A1 (chr9: 37544050-37582460) and the human/rat conserved regions (60% sequence identity over 90 bases) in MCS5A2 (chr9: 37586100-37658620) were resequenced in 24 women representative of the case-control population frequency of block 4.2 haplotype variants. DNA was submitted to Polymorphic DNA Technologies (Alameda, Calif.) for resequencing. The following polymorphisms had minor alleles that were observed in more than one individual, and were not listed on NCBI. Base pair positions in bold type are the SNP locations based on the human chromosome 9 May 2004 build at UCSC. The bolded IUPAC SNP symbol identifies each SNP.

MCS5A1 Polymorphisms
37645018
AATTCTCCTCGATGGAAACCTGAATTACTTTCAGTTTGGGGCTATTATGG
ATAATGCTGCTGTGAATATTCTTATATAAGTGTTTTTGTGGACACGTTTT
AATTTTTCTTGAGTCAATACTTAGGAGTGGAATTCCTAGGTTCTTTTCCC
AGAGAGGCTATACTATTTTACACGCCTACCAAGAAAGAWTAAGAAACACA
GTTGCTCCACATTTGTTGTGGTGTTTTTGTTTGTTTTTTGCAGGGTCACA
CTTTGTCAC
(SEQ ID NO: 124)

37546702
CTGAGTTCAAGCCATTCTCCTACCTCAGCCTCCCAAGTAGCTGGGATTAC
AGGTGTGTGCCGCCACGCCCRGCTAATTTTTGTATTTTTAGTAGATATGG

-continued
GGGTTTCACCATGTTGGCCAGGCTGGTTTTGAACTCCTGACATCAGGTGA
TCTGTCCGTCTTGTCCTCCCAAAGTGCTGGGATTACAGGCGTGAGCCACC
GCATCCAGCCTGTTCTGTATTCTTTAATGGAATATGTCA
(SEQ ID NO: 125)

37647001 24-131
AAACCACCAATCTGGATATTAGACATGCTTTTTCTACTGGCTTGGTCATT
GTTTCTAAGCCTTTTGCATCCTCCACTGGATTGTTTACGATAGGGACTGG
GTACTTTTCTCTCTGAAGACTCAATACCTGGYGTTGACTCCTTTCTCTAT
TACAACTATTCAGGGCAACAGAAAAGACAAGGAGAGCATTCTTAGCTACA
GGGTGCCTACATTATTCCAATACTGGGTCTACGTGTCCATGCACTATGAG
A
(SEQ ID NO: 126)

37551088, 37551094, 37551166
GGGCTTGCAGTGAGCCRAGTCRTGCCACTGCACTCTAGCCTGGGCGAAAG
AGCAAGACTCCGTCTCAAAAAAACAAAACAAAACAAAACAAAAYCAACTT
TTTTTTTTTTTTTTTTTTAAAGAAGTGAGGTCTCTCTGTGTTGCCCAGG
CTGGAGTACAGTGGCAGGATCATAGCTCACTGCAGCCTCGAACTCCTGGC
CACAAGTGATCCTCCCACCTTAGCCTCTCAAAATACTGTGATTA
(SEQ ID NO: 127)

37555869
CACTCGTTAGAGAGGTGCAGAACCACTGAAGCCCAGCCCGTCCCCAGAGA
CTCTTGTTTTTAACCACTAAGCCAAGCTTCATGGAGGAGCTGGTATCTGA
ACTGGACTCTGAAATTTGCATAGGACTGGGACATTCAGAGGAGGAAGAAA
GGGGGCTATRGCAGAGGAAACAGCATCAGCAAAAGCTCCTGAGGTAGAAA
ACCTTCAGCTGGGCTTAGGACATGTTGGGAGGTTCAGT
(SEQ ID NO: 128)

37558463, 37558666
CTCCTGACCTCAGGCAAACCGCCCACCTCAGCCTCCTAAAGTGCTSGGAT
TACAGGTGTGAGCCACTGGCACACATCCCCACCCACCCAATTTACTTTGT
TTTCAAGAAACCAATTTACTTTGTTTTCTCAGGTAAATTATTTACTCTCT
TCCTTTTTCTCTCTGTAGGCTAGTAAGACTCCAATCAAAGTTGATACATT
GTATTTACATCTCCTCTACCCTAAGGTGGAAAAAGGATAAACGGAGTTY
(SEQ ID NO: 129)

37560924
CTGAGGCAGGTGAATCACGAGGTCAAGAGATGGAGACCATCCAGACCAAC
GTGGTGAAACTCCGTCTCTACTAAAAATACAAAAAATTAGCTGGGCGTGG
TGGCACGTGCCTGTAGTCCCAGCTACTCAGGAGGCTGAGGCAGGAGAATC
GCTTGAAACCGGAAGGCGSAGGTTGCAGTGAGCTGAGATTGCGCCACTGC
AGTCCAGCCTGGCGACAGGGCAAGACTCCGT
(SEQ ID NO: 130)

37561238
CTCAAAAAAAAAAAAAAAATTATAAACAACTTTATATAAGTAAATATGA
AGGGATAAACTCCTAGGAAAATATTACTTAGTTAAGAAATTATAAAACA
AAATCACCCTAGAACCATTAAAGACATTGAGTCTGTGGTCAAAAATAAGA
TTGCAAAGAAAACACACCTGCGAGCCCAGGTGGCTTCATCACCAAGTTCT
ATCATACATTCAAGGGACAAAGAAGGGGAAACTAAAATGGATGGTGGAGA
KGATGATATGGGTATT
(SEQ ID NO: 131)

Indel 37563886^37563887
AAAATCTTAATCAAATGTCTCTTTGTGTACATTCCTTTATGTATACAGTA
TCAAACATTTTAGACGAGTGGAAACTAATAATCACTAAACTAAAAGA[AA
GA]GGGTAATGAGAGAAATTAGCAGACATTTCAAACAAAACCCATGACAG
GTAACTCAAGAATAGGTTCATTCATTAAGGCAAACTGAAAGAACAAAACA
CTTGTTCCATCTATTTCCTGACTGAAGCAGGTACAAGGAATTTGTTTACT
TCACATCTTCCTGTGAAAAG
(SEQ ID NO: 1)

37571387, 37571587
CCRATAACATAAAAAATAGATTAATATGTATTTTGTATCATTATCTATTA
TATACTGTATTCTTACAACACAGTAAGCTAGAGAAAATGTTAAGAAAATC
ACAGAGAGAAAAAGCATTGACAGTACTATACCGTATTTATTTAGATTCTA
AGTTTAGGTTGTCTGTTTACAAGATTAGTCGTGTCTGAAATCAGAGCAAC
TAMAGCTGCAGACCTCAATCTATAGTACATATCAAGAATTCAACTTTTTC
CTTTAATGTCATGACTTTTCTC
(SEQ ID NO: 132)

37572952
GGAACTGCAGTATACACAATAGCCAGCAGATGTCAGAATGGAATCTCTTA
AGACTCAAGTATGAAAACACAATAAATAACAGGAGTTTCTGGAAGGACTG
AGGCTTTCTTGCTCTTCTGTGCACAACACACTTCAGTCACACTGGTCTTT
CTTCCTCAAATACATCTGCTTTAACACTTTTTCAAAGATGCCCCGCTCTA

TCTGGCCAATTCCTATTCACCCAAACCTTACTYTATGTGTCTCTTCCTAA
GG
(SEQ ID NO: 133)

Indel 37576899^37576900
ATATACACTTACATACCCATAAAAAATAATAAAATTATTTTAAAACCTAC
AAAATTTGAGAAATAAAGATACAAGTTTCAAGTTTAAATAGGTTCACCAA
GTGCCCAC[AC]CACAGTGTATTAAAATAAACACACACTAAATGATGTCA
TCATGGAATATAAGCATACTAGGAACAAAGATCCTTGTTTCTCAGGAAGA
AATACTTAGTCCCACAAAAAAATCAGGAATCAGAATGATTTCAGATTTCT
CAGCAGCAACACTGAAAGCTAGAG
(SEQ ID NO: 134)

37577085
GCTTTGCTTTAAAATTCTGAAGGRAAATGATTGCTAATCTAGAACCCTAT
ATTCATCAAACTATAGAATAAAGACATTTTTAAGGCCAGGCACAGTGGCT
CATGCCTATAATCCCAGCACTTTGGGAGGCTGAGGTGGGCAGATTACCTG
AGGTCAGGAGTTCGAGCACCAGCCTGGCCAACATGGCAAAACCCTGTCTC
TACTAAAAATACAAAAATTAGCCAGGCGTGGTGGCACGTGCCTGTAAT
(SEQ ID NO: 135)

37579753
CAGCCTCCTGAATAGTTGGGACTATAGGCACATGCCACTATGCCTGGCTA
ATTTTTGTATTTTTTTAAAAGACGAGGTATCACCATGTTGCCAAGGCTGG
TCTTGAACTCCTGAGCTCRAACAATCTGCCCGCCTCAGCCCCGCAAAGTG
CTGGAATTACAGGCATGAGCCACTGCGCCCAGCTCAATTTCTTAATATTA
AACTGAAGACACTGAGATCTGTCAGAAGCTGATAAAGTCAGCA
(SEQ ID NO: 136)

37582143
AAAGTGCTGGGTGGGATTACAGGTGTGAGCCWACGCGCCCGGCAGCTCAA
ACATTCTTCAAGCTGGGAGAACCAGGATGATTAAACACGCGCGCCGGCCA
CCACGTGCACTTCAGTGCCCGGACCCTGACCCGCAGCACCTCAAACCGCG
CATATGCCCGTCGCCTTCAAGCGCACCCTCCTTGCTCCCCGCTACCGTTC
AGCTCAGTTCGAAGGCCCCGATG
(SEQ ID NO: 137)

37596576, 37596656
TTCTGGTGGCCCTGAGTTCTAAATTTTAAAGCCAAAGAGAGGTTGGTGTA
TAAAGCACCTCTTGCTAAATAGCGTTTTCTTCTGKACCACCACGCTGAA
TATGCACAACTCTTTTCTTTTCCCTCTTAGCTTGGCTGGAAATATAAAC
TAAAATTTACTTYAAAATTAATAGAAAACAAAAAAGAUCCCTTTAAA
(SEQ ID NO: 138)

37597576
AGGTCTGTGATTGTATGTGAYCTTAGTCATCTATTTGTTACACAAGCATT
TTTGGATTGTTTGAACCATTCAACACCTCTTTCCTTTGCATATATGGAGA
TTAGGAGGATTCTTAATAGGTAGTTATTTGAGCATCAAGCCTGTCATAGA
TATTAAGGAGAATTACAGGGTCGGGGATTTATAGTCAAAATTCAAAGAGA
TGTGAAAATAATGAGAAACCTCATGGTTTAGGTTTTGATGTTAGAAGCTC
GCTGCTTCAAAGATCTA
(SEQ ID NO: 139)

37599480
AAAGTTTAAAATGTCTAAAACTTGGCTCCTAATATTCCCTTCTCGTTCCT
CTGCCCCCAAGAAACTTCCTCCCCTTCAGTTTTCCTCATCTCAGGTAGCG
GCAAGTCCAGCCTTCAGGTTGCTGAGGCCCAAAACCTTGGAGTCATCTTT
GACTCATCTCTTTCTCTCAMACCCTGCATCCAATCTGGTCAGCAAATCCT
GTTGCTGCACCTTCATAAAGCATATCCAGAATCAGAGTACTTCTCACTCC
TC
(SEQ ID NO: 140)

37601836, 37601857
TTTGGAAACATTTTTGACATACCTTAGTGCACAGAGCTTAATGCAGAGCT
TGGCATACAGTAAGCCTTCAATGTCTATCTTCTGTATYCTTTTTTTCCCT
TTACTCCTKATCTTAGAATGTGCAGCATTTCACAGATCTGGTTATAATGA
CATTGGACCTAAAGTGATTCTCTCAGCCTAGGAGAGAGGCCAGTGGCGAT
(SEQ ID NO: 141)

37602870
AAGTATTTTAAAGGATTGAGTTCACTGGAGAGATGTCCTGTTTTTAAGT
GACTACGAGAACCTGGTCACTGTTYCCAATATCAGAAGGACTGCCACGGG
GCAGAGGATGAGGAGTTGTCCTTCATGGGTCCAGAGGGCAGAACTAGGAC
CAGTAGGGAGGTAGATGTTAACCTGAGAATGGGAAGAACTTTAATGGCTA
(SEQ ID NO: 142)

37603261
AAGGCAAGGTGATTTTTCATTTTCAAAAATAATTTATTGATTAATTACCT
ACCATGTGCAGGACATTGTCCTAAGTGCTAGAGGAGCCCAAATGTGAACT
AGGCAAGTAGTGTGCTCCTAGAGAGCTCCTGGTGTAAGAGGGAAGATAAA
AGTCATCTATCCATGCATCCATTCACTCAGTGAATATATACTGAGCACCT
(SEQ ID NO: 143)

37605662
CTGTTTCTTTAAGGTGACTTAGCAAATCTCTACTCTAATACATTATGTGT
TGATGTCCTATTTTAACTCTCAAGGACAATCTCATTTCTAATTCTTTCAG
GATCACTCACTGTTGCCCTTAGTACTGACAACACTTTACAGCCTCRAGAT
TT
(SEQ ID NO: 144)

37610247
AGGCTCATTTTCCTCATCTATAAAATAGGAATAAATACCCATATTCTTCAC
AGGGGCTGCTGTGAGAAYTAAATAACATGCACCATAAATCACTTAGTCCAG
CACCGGGCATAGAGAAGGCCCTAAGTAAATGGTTGCTATTGATCATCATG
ATTTAAAAAAAAAAAAAACTAAATAATGAGCAGTTTCGCCACTGACAAGG
CA
(SEQ ID NO: 2)

37610427
AGGCTCATTTTCCTCATCTATAAAATAGGAATAAATACCCATATTCTTCAC
AGGGGCTGCTGTGAGAAYTAAATAACATGCACCATAAATCACTTAGTCCAG
CACCGGGCATAGAGAAGGCCCTAAGTAAATGGTTGCTATTGATCATCATG
ATTTAAAAAAAAAAAAAACT
(SEQ ID NO: 145)

37611591
AAGAGGATTTCTTTGGAGGAAGCAGCTGGTGTGCTAAGTGCCGCTCATGG
CCCCAGGGGATAAGGAAGGGGTGTGTGGGTGCCTATCTCACCTCACTTCA
GCAGGACCACTCAGAGCTTGAGCTGTGTCTCCTGCAGTTGGGGGCCCAGG
GGACTGGGTCTGACTCCCRCCCTGGAAATTTACAGGAAAAGAGCAGGGCT
GGCTAATGCTTTGGCTG
(SEQ ID NO: 3)

37616956, Indel 37617088^37617090
GAAGTTCGAGCAGTACTGGTTTAGAGTACACCTGCTTTGCAAGTGATWGT
AAGTGTGTCTTCATTCCCTTTAATGTAACAGAGCTCCACACATAATTGGA
CTATGTAGTCATTGCCAGTTACTCCACCTTCGAGGCGATCTTTGCTGACT
CAGGTTTTCCTGCGTTTTCCCAGAGCTG[TTT/*]CTTTCAGCTCCCATG
GTC
(SEQ ID NO: 146)

37618560
CAGAGAAAAGAAAGGAGGAGGAGGAGGAAAGAGAAGTCAAGTTTTTAAA
AGCAAACAGAAATAATAGTTTTGATGGGATGGATTTGTTTTCTTAATAAG
CCTAATGATCCCAGGAKTCTCATTGGATTATTAGCAACTGTATTTAAAAT
TTAAATCTAAAACAAGTTTTGTAGCTGCAAAGTGCTTATCAGAACCTAAC
CATGCCTCTCTGGCT
(SEQ ID NO: 4)

37618765
CTTATCAGAACCTAACCATGCCTCTCTGGCTGGCGGCTAAGGGAACCTGC
CTACCTGAGGGATGGCCACTTGATGTAGCATAGTGAGGAGAAGGGACTTA
GGCCTGACTTGACCAAAATCTTAGTGTGATCTTTCSCAAGCTCCTTCCTC
CTTCCCTTCCTGGTGCTGCAGCGTCTTCCCTATAAAATGAATAATGGA
(SEQ ID NO: 147)

37619515, 37619523
ACTAGATGACCGATTGTAGGCASGCCAATTRCATGCTCAGGGCAGTAGCA
ATGCAGGGCCACCCGCCAACATCATTTTGTCTGGAAAACATTTGATACCT
GATGCTTTCCTAAAACATTAAAGTAATCCTCACAGGAAATATCAGAACT
TTACTGGACCTCTTTTATACTTAGTTTATAGTTCAGTGCTTTTTAAAAAAA
(SEQ ID NO: 148)

37634719
AGAGCTCAGTTTCCCAAATAAACCTGAATCTGAATCCCATTTACCAGCTC
TGTGACCTCATACCAGTCGYTTGAATTCTCTGAGCTTGCCTCAGTTTCAT
CTGTGAAGTGGGGATTGTCATGTGTGTCCTGCCTAACTCAAGCAGCTGTT
GAGAGAATAAGATGAGATGATTGCTCTGTTTGGTGTTTTACAAACTGAAA
(SEQ ID NO: 5)

37635098
TAGTGCTAGAGAGGGTGGCATCTGCCCCCGGGGGCTGTGGGGAGCACGGT
GGTAGTGGGGAGTTGCAGTCACCCAGCAGATGCAAAGCAGAATGAAGCCT
ATGGGAAGTGGCCAGATGTAGTTGTCAAGACCAGGGTAGGGCCACACTTG
ATGCTGGCCACAACCTCAAGCACATGCCTTCTTCTGGGGAGCTGATCTCCC
AGGAGCTGAGCCAGCAGRAAAAAAAAAAAAAGAGAG
(SEQ ID NO: 6)

-continued

37639129
AGGCTGACACTGACGCAGGTAGCTAGGAAATGGAGGGGGACAGGGCAAAA
TTCCATGGGAACATTTGTACTCACCRGACAAGAGAATAGTTCTTATCTT
ACTTTCTGACAAGTGCTATGCTTTTTGGTGTTTAACTGCCTTGGAGAGAG
TAATTTGATGATTAATCTTTATCTACAAAATAATTTTTAAAATTAAACTT
TATTTTGAGAAAATTGTAGATTCA
(SEQ ID NO: 7)

37639690
AAGTGCTGCTAGTCTTCCCCCACCGCCCTTGGATGAAGGATGCACUGUAA
CATCTGCCTGTGCRCCATCCCCAGAATGATCTAACATCCCAGTCTGATGG
TGCCTCAACCCTACTCAGAACTCCTCCCATGAACCTGCCAGTGCACTGGG
AACACGGTGCAAACTCCTTGACCAGGAATTGGCCCCTGGTGACTCCCC
(SEQ ID NO: 8)

37641238
CTCGTGTCCCAAAAGCCCGGCTCGGGGCGCGTCCGTGGGCTAGCTCAGG
ACCTGCCATCGTGAACTGTTTGCACAGTAGCGATGTGTGCUAAGTTTGCG
AGATCTGCATGGTGTAGTGAGTGGAAACAGCGGCAACGCGGGAGGGGAG
AGACCTGGGTTCAGGTGCGGCCGCGGCCAGCGCCAACTTTCTGAGTGACC
TCAGACCAACCCTCTCTGTCCGTCCTCGATGGC
(SEQ ID NO: 149)

37642526
GATTTTATTTCCTTCCTCRACATCCTGGTTTTAAGTTTCTAGCATTATGA
AATCAGAGAGCTGGTGAGGGTGTGCTTGGTGACCAGAGCAGAGTTGTGGT
ACCTAAGTTTGTCTTTCCTGAATGAGACCCCATCCTTGAAGCTAATTTTG
TCCAGAGCCTTTTTATCTCTCTGACGCATTCAAATGCCA
(SEQ ID NO: 150)

37643111
AGGTGGTGAGGAATAGAAAGGCTATGTGTAGGTCAAGGAGCTGGTACGAG
CAAGGAACTGGTGAGAGCTGGGAGAGCATGAGACAGATGAGACAGTGAG
CCTGGTGGAAGCACAGAGAAGGCAGAGCACTTCAGAGACAGGGCAGCGGG
ARGAGGCTCTGGAGGCTCTGAACCTGGGCTGGAATCCTCGCTGGCTGTGG
(SEQ ID NO: 9)

37648196
TTATTACAAAGTTCTTCATTATTCCAAGCCAAAAATCTTCCTCTCGGCAA
TGGTTGCCCCATTGGCCCGATCCTGTCCTTTGAAGCCCCACACACAAAAA
ATCCATTTCTTCTTCCCTATGACAGCTAGTTAGGCCACTTGGACCTTCAA
AGACAGGGATCAGGCCCCCCACATCTTCACTTTCTTTTAGGCAGAATGCC
CACTTTATCTGGCCCCTCGAAAAGCTAAGAATGGGACACCGCTGTGCAGG
TGGGGGTCTGATCAGCCCAGAYAGGAGCAAGCCCACTGGAGCCTCACTTC
GGAATCTATATTTTGCGTTAG
(SEQ ID NO: 151)

37650583
ATTTCTCTTAAAGAACAGTGATTTTAAAGTAGGTTTTAACAAYGGGTTTA
AAGAACAGTGATTTTCCATTTTGACAAGGCTTGTTTGGTATAGCCACTTC
AAAATATCCCCACATCAAAATATGATGCTTTATCTGGGATATCTTTTCCA
GACTTTGGGAGCCTTCCCTCCTGCACTTTCATTTCTGCAAGGCAATACTC
(SEQ ID NO: 10)

37650831, 37650879
TGGGCAGGGACCGAGCCTTGCTGCTCATTYAGTACGGAGCCCAGAAGGAG
GCCTGGGGGGTACAGTGTTGACCGATGRAATGAATGAATGCATGGCTATG
ACTACTTCCTTAGCTGCATCTGGCTCCCAGCTGCCTTCATTGGTCTCTAC
AGTCATCAGTAGTATCCTGGCTAAGTCAAGAGCATATGTGGGCCTCTGTG
(SEQ ID NO: 152)

37653206
GATGCGTACAACCTGTGCACACTCATCCCTCTCTTGTATTTAGTCTGCCC
AATTTAATTTGTTTAGATACCGTAGGCTTTTATTGATTGCCCATTAGAAG
TTTAGCCTAGTGTTGACAGCCTAGGGGTATAAGAGACATCATTAGCCAGA
AATTTCTTTTGTAGCTGGACTAGTAAGTCTTATACCCAAGAGTCAGTGAA
CAGAATKATCTGTTCACTGGGGATTGCTGAGTAAATTGGTGTGAGTGCCA
GGATTTCTGCCCCAGGCTGAGAGATGTGGATAGATGGATGCTGAAGATGG
TTCTTCAGGAAGTCTTTTGGAGGAGTCTGCATTGGAGATGGGCCAGGTGG
GGATTGCATGCCAGAGTGGAGATGCAGGGGGAGGGGGCTGATCAGCAGGT
(SEQ ID NO: 153)

37655211
CAACATATTTGTAATACAGACATCGAAAATAAACCAAATATCCAGCAATA
GGGACTTAGCTTTAAAAATGGCACTGTTATCTATAGCAAATAAACAATAA
TGTTGTAGAATAATAAAGCACAGGGAAATGTTTACAGTGTATATTTTT
CAGTTTAGAAACCAGCATATATGGTAAGTTCCCAATTATGTTGAAAATGT
GTCTTTTCACACWAAAAGACTGGAAGAGTAATTAGCAACTTATAGCTTTT
AGTGGACAATTTTTATTATCTTCTCTCCAAAAAAGAAAACTTTCAAAATT
TTCTACCAGCCACATGTATTACTTTTATAAGAGGGAGGAAATAAGTGACA
ATTAAGAAAAAGAGATAAGCTTTTGGAGAGCGTTGTTTGAGCGTCACTAG
G
(SEQ ID NO: 11)

37655573
TGGAAAACTAAATGAGCACATCATTTATCTTGCAAATTCCAGACAGGTGG
TGTTTTCAGAAGGAAGAGTGGTCTTAGGTCCATTTGTGTGAGTATATTTA
TAGAAGTGAAAGCTTTGGGGGAAGGAAATAGATTGATTTTTTTCCCCTT
GAACTTCTGAAATTATTTTTTCCRCTCCATTTGTAATTGAGCCCAGGGAG
CTATTCTTATTTCTTCCTTTTCTTGGGCACTGCGTTAGACCTAAAAATGT
TAACTGGCTTAGGATGTGGGTTTTGCTAAAATGATTCCCCTTTGAAGTCT
TCACTGGGCTTTCTCATGCTTAAAAGTGGGGTCCCGCAGAAGATCACTTT
CTACCTAATGCACTTTGCTCCTGAAGTCTTTGGCAACGTTGGGGTGGTCA
GA
(SEQ ID NO: 12)

SNPs identified as having variation in the Wisconsin population were compiled after resequencing. The distribution of minor alleles for each SNP in the 24-member group was compared to the distribution of the haplotype block 4.2 alleles. SNPs with minor alleles that were only found in individuals carrying a copy of block 4.2 allele 4 were determined to be correlated to rs2182317 (the minor allele of SNP rs2182317 is only found in block 4.2 allele 4). SNPs at different locations were put in the same "bin" if the minor alleles were distributed similarly among the 24 women resequenced. (All SNPs highly correlated to rs2182317 were found only in the orthologous region to the rat Mcs5a2 locus.)

Definition of Blocks 4A, 4B, and 4C

New blocks A, B, and C, based on the distribution of minor allele patterns observed after resequencing, were defined in the regions that were previously called blocks 4 and 5. Because $r^2$ does not relate to distance, polymorphism bins are of different sizes and multiple bins overlap each other. Blocks were defined as regions that exclusively contained sets of minor allele distribution patterns. Even though D' values across the entire region are 1 for many pairs of SNPs, $r^2$ values are very high for groups of SNPs only within the blocks. These blocks are based on the distribution of the SNP minor alleles instead of the D' values used in earlier versions of the map.

Genotyping New SNP Bins Identified after Resequencing

Seven polymorphisms from five additional SNP bins, located in MCS5A1, were genotyped in the Wisconsin samples. The primers are as follows:

```
indel 138-9899
(chr9: between 37,563,887 and 37,563,888)
forward primer-TCAAACATTTTAGACGAGTGGGAAACT
(SEQ ID NO: 154),
reverse primer-TGAGTTACCTGTCATGGGTTTTGTT
(SEQ ID NO: 155),
VIC-CTCATTACCCTCTTTCTTTT(SEQ ID NO: 156),
FAM-TCTCTCATTACCCTCTTTT(SEQ ID NO: 157);

rs6476640
forward primer-TCCCATAGTATCCAGCACTGACA
(SEQ ID NO: 158),
reverse primer-AGCCTAGGGTATTCATTATTGATGAGCTA
(SEQ ID NO: 159),
VIC-ATCTGGGAGAGAAAT(SEQ ID NO: 160),
FAM-ATCTGGGACAGAAAT(SEQ ID NO: 161);

rs10973418
forward primer-GGGAAACAAACCAATAATAATGGAAGACAA
(SEQ ID NO: 162),
reverse primer-GGGAGCACATTTTGAGTTGTAAGG
(SEQ ID NO: 163),
VIC-AGCAGGTAGCTTTT(SEQ ID NO: 164),
```

-continued
FAM-CAGCAGATAGCTTTT(SEQ ID NO: 165);

24-131 (chr9: 37548802)
forward primer-GGACTGGGTACTTTTCTCTCTGAAG
(SEQ ID NO: 166),
reverse primer-CTTGTCTTTTCTGTTGCCCTGAAT
(SEQ ID NO: 167),
VIC-AGTCAACACCAGGTATT(SEQ ID NO: 168),
FAM-CAACGCCAGGTATT(SEQ ID NO: 169);

rs7021977
forward primer-GGGCCACGTAGATGAGAAAGTT
(SEQ ID NO: 170),
reverse primer-GGAAGATGCGCGAGGATGT
(SEQ ID NO: 171),
VIC-CCGTATGGAGGAGATC(SEQ ID NO: 172),
FAM-CGTATGGAAGAGATC(SEQ ID NO: 173);

rs6476643 (SNP-A1)
forward primer-TGGGCTTCCCGACCAC(SEQ ID NO: 174),
reverse primer-CCGGTGCCCCTCCTG(SEQ ID NO: 175),
VIC-CAGATACAGCTTTTATGCGC(SEQ ID NO: 176),
FAM-AGATACAGCTTTTCTGCGC(SEQ ID NO: 177);

128-249
Forward primer-CATCTCCTCTACCCTAAGGTGGAAA
(SEQ ID NO: 178),
Reverse Primer-CGACCTTAGACCACGTGAACTC
(SEQ ID NO: 179),
VIC-ACCACATGAACTCC(SEQ ID NO: 180),
FAM-ACCACATAAACTCC(SEQ ID NO: 181);

rs10117312
Forward Primer-CCTTCGGAGGCCTTGGAT
(SEQ ID NO: 182),
Reverse Primer-CTTTGTGAGGAGAAAAGCAACATTCA
(SEQ ID NO: 183),
VIC-CTGCCTCTGATTATT(SEQ ID NO: 184),
FAM-TCTGCCTCTAATTATT(SEQ ID NO: 185).
SNPs were run using ABI Assays-by-Design.

SNP 10117312 was not used in an association test because it has an $r^2$ of 1 with rs6476640. These data are uncorrected for multiple comparisons, because only one SNP (rs6476640) was tested in the combined Wisconsin and UK populations. SNP rs6476643 (SNP-A1) was analyzed in the Wisconsin population along with the SNPs, where it is subjected to the same battery of statistical tests described above.

Quality Control for Human Sample Genotyping

Quality control of the Wisconsin samples was conducted with DNA from 85 subjects who had submitted two independent samples. These duplicate samples were genotyped for all polymorphisms tested in the entire Wisconsin population; 95% (1648/1729) of the genotypes were identical for the two samples, 5% (81/1729) of the samples had a call for one, but a no call for the other sample. There were no sample sets that resulted in mismatched calls. Wisconsin samples that were genotyped twice (initially when the original haplotype block map was made and again when a subset of these SNPs was genotyped in the entire population) yielded the same genotype 98.4% (1794/1823) of the time. Only, 1.5% (27/1823) had a no call in one of the replicates. Mismatches occurred in 0.1% (2/1823) of the replicates. Due to a small number of women of non-European descent in the Wisconsin set (73 cases, 90 controls), and an effort to avoid population stratification, these samples were not included in the study. For the UK samples each 384-well plate had 12 samples that were duplicated on a separate plate. All genotyping calls for the first four SNPs tested in the UK population were in agreement for each duplicate, except for one genotype of an individual with no call. The call rate for SNP rs6476643 was 0.981 in the UK study set.

We claim:

1. A method of analyzing invasive breast cancer susceptibility or resistance, comprising the steps of
   a) obtaining a DNA sample from a female human patient,
   b) genotyping the sample for the presence of the minor allele of rs2182317 wherein G is substituted with T on the plus strand, and
   c) analyzing invasive breast cancer susceptibility or resistance by correlating the identity of the allele with risk assessment data, wherein the presence of the minor allele of rs2182317 indicates a decreased risk of invasive breast cancer compared to a patient who does not have the minor allele of rs2182317 of step (b).

2. The method of claim 1 wherein the DNA sample is collected from mouthwash after the patient has rinsed his or her mouth with mouthwash.

3. The method of claim 1 wherein the patient is found heterozygous or homozygous for the minor allele at rs2182317.

4. The method of claim 3 wherein the correlation indicates that the patient has a 14% reduction in risk compared to a patient who does not have the minor allele at rs2182317.

5. The method of claim 1, wherein step (b) further comprises genotyping the DNA sample for the presence of at least one minor allele selected from the group consisting of

| Allele | Minor allele on the plus strand |
|---|---|
| 114-117 | T |
| d3-169 | A |

-continued

| Allele | Minor allele on the plus strand |
|---|---|
| rs12378421 | G |
| r3-116 | T |
| rs17505776 | C |
| rs4878708 | A |
| rs4878709 | A |
| rs4878710 | A |
| rs10973450 | C |
| 14-70 | T |
| m4-218 | G |
| rs4490927 | T |

-continued

| Allele | Minor allele on the plus strand |
|---|---|
| x4-77 | A |
| z4-66 | G |
| f5-152 | G |
| rs4878713 | G |
| y5-43 | C |
| i6-31 | T |
| I6-103 | G. |

* * * * *

UNITED STATES PATENT AND TRADEMARK OFFICE
CERTIFICATE OF CORRECTION

PATENT NO.         : 7,858,303 B2
APPLICATION NO.    : 11/374326
DATED              : December 28, 2010
INVENTOR(S)        : Gould et al.

It is certified that error appears in the above-identified patent and that said Letters Patent is hereby corrected as shown below:

Column 18, line 4 "5'-CGCCTACACCTMGCATGAG (SEQ ID NO:26)," should be "5'-CGCCTACACCTTTGCATGAG (SEQ ID NO:26)"

Column 20, line 7 "reverse primer-ACACAATTTAAAATAACUGAGGCAGCAAG" should be "reverse primer-ACACAATTTAAAATAACTTGAGGCAGCAAG"

Column 21, line 28 "VIC-CCACTTTGAAGTGTTCTGT (SEQ ID NO: 86) should be "VIC-CCACTTTGAAGTGTTCTGT (SEQ ID NO: 86)"

Signed and Sealed this
Fourteenth Day of June, 2011

David J. Kappos
*Director of the United States Patent and Trademark Office*